(12) United States Patent
Dunn et al.

(10) Patent No.: US 6,642,241 B1
(45) Date of Patent: Nov. 4, 2003

(54) ALKYLAMINO-SUBSTITUTED BICYCLIC NITROGEN HETEROCYCLES

(75) Inventors: James Patrick Dunn, Los Altos, CA (US); David Michael Goldstein, San Jose, CA (US); William Harris, Bedfordshire (GB); Ian Edward David Smith, Bedfordshire (GB); Teresa Rosanne Welch, Sunnyvale, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/693,364

(22) Filed: Oct. 20, 2000

Related U.S. Application Data
(60) Provisional application No. 60/213,718, filed on Jun. 22, 2000, and provisional application No. 60/160,804, filed on Oct. 21, 1999.

(51) Int. Cl.[7] ............... C07D 487/04; A61K 31/519; A61P 9/10; A61P 11/06; A61P 17/04
(52) U.S. Cl. ...................... 514/258; 544/256
(58) Field of Search ............. 544/256; 514/258

(56) References Cited

U.S. PATENT DOCUMENTS

| 5,162,316 A | 11/1992 | Coates | 544/256 |
| 6,150,373 A | 11/2000 | Harris et al. | 544/256 |

FOREIGN PATENT DOCUMENTS

| EP | 0 351 058 B1 | 6/1993 |
| WO | WO 96/34867 | 4/1996 |
| WO | WO 99/61444 | 12/1999 |

OTHER PUBLICATIONS

Graninger et al. Curr. Opin. Rheumatol. 13(3): 209–213, 2001.*

* cited by examiner

*Primary Examiner*—Richard L. Raymond
*Assistant Examiner*—Venkataraman Balasubramanian
(74) *Attorney, Agent, or Firm*—Robert C. Hall; Rohan Peries

(57) ABSTRACT

Alkylamino-substituted dihydropyrimido[4,5-d] pyrimidinone derivatives are provided which are useful as inhibitors of p38, along with a process for their manufacture and pharmaceutical preparations containing them.

22 Claims, No Drawings

ALKYLAMINO-SUBSTITUTED BICYCLIC NITROGEN HETEROCYCLES

CROSS-REFERENCE TO RELATED APPLICATION

This application claims the benefit under 35 U.S.C. 119(e) of U.S. Provisional Application Serial No. 60/213,718, filed Jun. 22, 2000, and U.S. Provisional Application Serial No. 60/160,804, filed Oct. 21, 1999, each incorporated herein by reference in its entirety.

FIELD OF THE INVENTION

The present invention relates to bicyclic nitrogen heterocycles. More particularly, the invention is concerned with alkylamino-substituted dihydropyrimido-[4,5-d] pyrimidinone derivatives, a process for their manufacture and pharmaceutical preparations containing them.

BACKGROUND OF THE INVENTION

Mitogen-activated protein kinases (MAP) are a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group which includes various isoforms (e.g., p38α, p39β and p38γ). The p38 kinases are responsible for phosphorylating and activating transcription factors as well as other kinases, and are themselves activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

The inhibition of these cytokines by inhibition of the p38 kinase is of benefit in controlling, reducing and alleviating many of these disease states.

SUMMARY OF THE INVENTION

In one aspect, the present invention provides compounds represented by the formula:

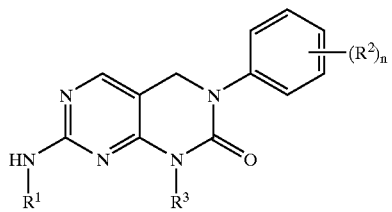

in which:

the subscript n represents an integer of from 0 to 3, preferably 1 or 2;

$R^1$ represents hydrogen, alkyl, alkenyl, alkynyl, alkylcarbonyl, cycloalkyl, cycloalkenyl, cycloalkylalkyl, cycloalkylalkenyl, cycloalkylalkynyl or aralkyl;

each $R^2$, when present, independently represents alkyl, halo, heteroalkyl, or vinyl;

$R^3$ represents heteroalkyl, heteroalkenyl, heteroalkynyl, heteroalkylcarbonyl, heterosubstituted cycloalkyl, heterosubstituted cycloalkylalkyl, heterosubstituted cycloalkylalkenyl, heterosubstituted cycloalkylalkynyl, heteroalkylsubstituted cycloalkyl, heterocyclyl, heterocyclylalkyl, arylheteroalkyl, heteroarylheteroalkyl, -(alkylene)-C(O)$R^{31}$ or -(heteroalkylene)-C(O)$R^{31}$;

wherein $R^{31}$ represents alkyl, haloalkyl, hydroxy, alkoxy, amino, monosubstituted amino, disubstituted amino, cycloalkyl, cycloalkylalkyl, aryl, aralkyl, heteroaryl, or heteroaralkyl;

and their pharmaceutically acceptable salts.

In another aspect, the present invention provides compositions comprising a pharmaceutically acceptable excipient and a compound of formula I, above.

In yet another aspect, the present invention provides methods of preparing the compounds described above. Briefly, the methods involve either:

(a) treating a compound of formula II

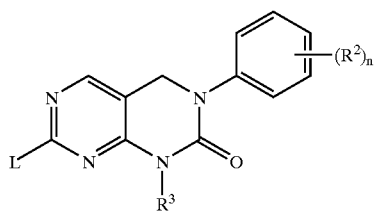

wherein n, $R^2$ and $R^3$ have the meanings provided in claim 1, with the proviso that any interfering reactive group present is optionally in protected form, and L is a leaving group, with an amine of formula III $R^1$—NH$_2$ 

wherein $R^1$ has the meaning provided with reference to formula I above, with the proviso that any interfering reactive group present is optionally in protected form, and where required, deprotecting any protected reactive groups. or (b) treating a compound of formula IV

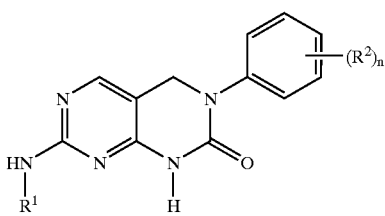

(IV)

wherein R¹, n, and R² have the meanings provided for formula I, with the proviso that any interfering reactive group present is optionally in protected form,
with an alkylating agent of formula V

(V)

wherein R³ has the meaning provided with reference to formula I, and X is a leaving group or a hydroxy group that is activated during the reaction, with the proviso that any interfering reactive group present is optionally in protected form, and where required, deprotecting any protected reactive groups.

The compounds of formula I and their aforementioned salts are inhibitors of protein kinases, and exhibit surprisingly effective activity against p38 in vivo. Interestingly, the compounds of formula I do not exhibit activity against the T-cell tyrosine kinase p56$^{lck}$ at levels below about 10 μM. The compounds can be used for the treatment of diseases mediated by the pro-inflammatory cytokines such as TNF and IL-1.

Accordingly, the present invention provides methods for the treatment of p38 mediated diseases or conditions in which a therapeutically effective amount of a compound of formula I is administered to a subject in need of such treatment.

In still another aspect, the present invention provides methods of preparing medicaments useful for the treatment of the p38 mediated diseases and conditions.

DESCRIPTION OF THE INVENTION
Abbreviations and Definitions
As used herein:

"Alkyl" means a linear saturated monovalent hydrocarbon radical of one to six carbon atoms or a branched saturated monovalent hydrocarbon radical of three to six carbon atoms, e.g., methyl, ethyl, n-propyl, 2-propyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Cycloalkyl" refers to a saturated monovalent cyclic hydrocarbon radical of three to seven ring carbons. The cycloalkyl may be optionally substituted independently with one, two, or three substituents selected from alkyl, optionally substituted phenyl, or —C(O)R (where R is hydrogen, alkyl, haloalkyl, amino, monsubstituted amino, disubstituted amino, hydroxy, alkoxy, or optionally substituted phenyl). More specifically, the term cycloalkyl includes, for example, cyclopropyl, cyclohexyl, phenylcyclohexyl, 4-carboxycyclohexyl, 2-carboxamidocyclohexyl, 2-dimethylaminocarbonyl-cyclohexyl, and the like.

"Cycloalkenyl" means an unsaturated non-aromatic monovalent cyclic hydrocarbon radical of three to seven ring carbons. Representative examples include cyclohexenyl and cyclopentenyl.

"Cycloalkylalkyl" means a radical —R$^a$R$^b$ where R$^a$ is an alkylene group and R$^b$ is a cycloalkyl group as defined herein, e.g., cyclopropylmethyl, cyclohexylpropyl, 3-cyclohexyl-2-methylpropyl, and the like.

"Acyl" means the group —C(O)R', where R' is alkyl, haloalkyl, heteroalkyl, aryl, heteroaryl, aralkyl or heteroaralkyl.

"Alkoxy", "aryloxy", "aralkyloxy", or "heteroaralkyloxy" means a radical —OR where R is an alkyl, aryl, aralkyl, or heteroaralkyl respectively, as defined herein, e.g., methoxy, phenoxy, pyridin-2-ylmethyloxy, benzyloxy, and the like.

"Halo" or "Halogen," means fluoro, chloro, bromo, or iodo, preferably fluoro or chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like, and further includes those alkyl groups such as perfluoroalkyl in which all hydrogen atoms are replaced by fluorine atoms.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Monosubstituted amino" means a radical —NHR where R is alkyl, heteroalkyl, haloalkyl, cycloalkyl, cycloalkylalkyl, aryl, aralkyl, aralkenyl, heteroaryl, heteroaralkyl, heteroaralkenyl, heterocyclyl, or heterocyclylalkyl, e.g., methylamino, ethylamino, phenylamino, benzylamino, and the like.

"Disubstituted amino" means a radical —NRR' where R and R' are, independently of each other, alkyl, heteroalkyl, haloalkyl, cycloalkyl, cycloalkylalkyl, aryl, aralkyl, aralkenyl, heteroaryl, heteroaralkyl, heteroaralkenyl, heterocyclyl, or heterocyclylalkyl, or R and R' together with the nitrogen atom to which they are attached form a heterocyclyl ring. Representative examples include, but are not limited to, dimethylamino, methylethylamino, di(1-methylethyl)amino, piperazin-1-yl, and the like.

"Aryl" means a monovalent monocyclic or bicyclic aromatic hydrocarbon radical of 6 to 10 ring atoms which is substituted independently with one or more substituents, preferably one, two, or three substituents selected from alkyl, haloalkyl, heteroalkyl, halo, nitro, cyano, methylenedioxy, ethylenedioxy, cycloalkyl, optionally substituted phenyl, heteroaryl, haloalkoxy, optionally substituted phenoxy, heteroaryloxy, —COR (where R is alkyl or optionally substituted phenyl), —(CR'R")$_n$—COOR (where n is an integer from 0 to 5, R' and R" are independently hydrogen or alkyl, and R is hydrogen, alkyl, cycloalkyl or cycloalkylalkyl) or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl or cycloalkylalkyl, or R$^a$ and R$^b$ together with the nitrogen atom to which they are attached form a heterocyclyl ring). More specifically the term aryl includes, but is not limited to, phenyl, 1-naphthyl, and 2-naphthyl, and the derivatives thereof.

"Aralkyl" means a radical —R$^a$R$^b$ where R$^a$ is an alkylene group and R$^b$ is an aryl group as defined herein, e.g., benzyl, phenylethyl, 3-(3-chlorophenyl)-2-methylpentyl, and the like.

"Aralkenyl" means a radical —R$^a$R$^b$ where R$^a$ is an alkenylene group and R$^b$ is an aryl group as defined herein, e.g., 3-phenyl-2-propenyl, and the like.

"Arylheteroalkyl" means a radical —R$^a$R$^b$ where R$^a$ is an heteroalkylene group and R$^b$ is an aryl group as defined herein, e.g., 2-hydroxy-2-phenylethyl, 2-hydroxy-1-hydroxymethyl-2-phenylethyl, and the like.

"Optionally substituted phenyl" means a phenyl ring which is optionally substituted independently with one or more substituents, preferably one or two substituents selected from alkyl, haloalkyl, heteroalkyl, halo, nitro, cyano, methylenedioxy, ethylenedioxy, cycloalkyl, cycloalkylalkyl, —COR (where R is alkyl or optionally substituted phenyl, —(CR'R")$_n$—COOR (where n is an integer from 0 to 5, R' and R" are independently hydrogen or alkyl, and R is hydrogen, alkyl, cycloalkyl or cycloalkylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl or cycloalkylalkyl, or R$^a$ and R$^b$ together with the nitrogen atom to which they are attached form a heterocyclyl ring).

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, heteroalkyl, halo, nitro, cyano, cycloalkyl, cycloalkylalkyl, —COR (where R is alkyl or optionally substituted phenyl, —(CR'R")$_n$—COOR (where n is an integer from 0 to 5, R' and R" are independently hydrogen or alkyl, and R is hydrogen, alkyl, cycloalkyl or cycloalkylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl or cycloalkylalkyl, or R$^a$ and R$^b$ together with the nitrogen atom to which they are attached form a heterocyclyl ring). More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heteroaralkyl" means a radical —R$^a$R$^b$ where R$^a$ is an alkylene group and R$^b$ is a heteroaryl group as defined herein, e.g., pyridin-3-ylmethyl, 3-(benzofuran-2-yl)propyl, and the like.

"Heteroaralkenyl" means a radical —R$^a$R$^b$ where R$^a$ is an alkenylene group and R$^b$ is a heteroaryl group as defined herein, e.g., 3-(pyridin-3-yl)propen-2-yl, and the like.

"Heterocyclyl" means a saturated or unsaturated non-aromatic cyclic radical of 3 to 8 ring atoms in which one or two ring atoms are heteroatoms selected from NR (where R is independently hydrogen or alkyl), O, or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, haloalkyl, heteroalkyl, halo, nitro, cyano, hydroxy, alkoxy, amino, monosubstituted amino, disubstituted amino, —COR (where R is alkyl or optionally substituted phenyl), —(CR'R")$_n$—COOR (n is an integer from 0 to 5, R' and R" are independently hydrogen or alkyl, and R is hydrogen, alkyl, cycloalkyl or cycloalkylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl or cycloalkylalkyl, or R$^a$ and R$^b$ together with the nitrogen atom to which they are attached form a heterocyclyl ring). More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, , pyrrolinyl, imidazolinyl, and the derivatives thereof.

"Heterocyclylalkyl" means a radical —R$^a$R$^b$ where R$^a$ is an alkylene group and R$^b$ is a heterocyclyl group as defined herein, e.g., tetrahydropyran-2-ylmethyl, 4-methylpiperazin-1-ylethyl, 3-piperidinylmethyl, and the like.

"Heteroalkyl" means an alkyl radical as defined herein with one, two or three substituents independently selected from —OR$^a$, NR$^b$R$^c$, and —S(O)$_n$R$^d$ (where n is an integer from 0 to 2). R$^a$ is hydrogen, alkyl, haloalkyl, cycloalkyl, cycloalkylalkyl, heterocyclyl, heterocyclylalkyl, aryl, aralkyl, heteroaryl, heteroaralkyl, alkoxycarbonyl, aryloxycarbonyl, carboxamido, or mono- or di-alkylcarbamoyl. R$^b$ is hydrogen, alkyl, haloalkyl, cycloalkyl, cycloalkylalkyl, heterocyclyl, heterocyclylalkyl, aryl, aralkyl, heteroaryl or heteroaralkyl. R$^c$ is hydrogen, alkyl, haloalkyl, cycloalkyl, cycloalkylalkyl, heterocyclyl, heterocyclylalkyl, aryl, aralkyl, alkylsulfonyl, alkoxycarbonyl, aryloxycarbonyl, carboxamido or mono- or di-alkylcarbamoyl. R$^d$ is hydrogen (provided that n is 0), alkyl, haloalkyl, cycloalkyl, cycloalkylalkyl, heterocyclyl, heterocyclylalkyl, aryl, aralkyl, heteroaryl, heteroaralkyl, amino, monsubstituted amino, disubstituted amino, or hydroxyalkyl. Representative examples include, for example, 2-methoxyethyl, benzyloxymethyl, thiophen-2-ylthiomethyl, 2-hydroxyethyl, and 2,3-dihydroxypropyl.

"Heteroalkylene" means a linear saturated divalent hydrocarbon radical of one to six carbons or a branched saturated hydrocarbon radical of three to six carbon atoms with one, two or three substituents independently selected from —OR$^a$, —NR$^b$R$^c$, and —S(O)$_n$R$^d$ (where n is an integer from 0 to 2) where, R$^a$, Rb, Rc, and R$^d$ are as defined herein for a heteroalkyl radical. Examples include, 2-hydroxyethan-1,1-diyl, 2-hydroxypropan-1,1-diyl and the like.

"Heterosubstituted cycloalkyl" means a cycloalkyl group wherein one, two, or three hydrogen atoms are replaced by substituents independently selected from the group consisting of hydroxy, alkoxy, amino, monsubstituted amino, disubstituted amino, or —SO$_n$R (where n is an integer from 0 to 2 and R is hydrogen (provided that n is 0), alkyl, haloalkyl, cycloalkyl, cycloalkylalkyl, heterocyclyl, heterocyclylalkyl, aryl, aralkyl, heteroaryl, heteroaralkyl, amino, monosubstituted amino, disubstituted amino, or hydroxyalkyl). Examples include 4-hydroxycyclohexyl, 2-aminocyclohexyl, "Heteroalkylsubstituted cycloalkyl" means a cycloalkyl group wherein one, two, or three hydrogen atoms are replaced independently by heteroalkyl groups. Examples include 1-hydroxymethyl-cyclopent-1-yl, 2-hydroxymethyl-cyclohex-2-yl and the like.

"Leaving group" has the meaning conventionally associated with it in synthetic organic chemistry i.e., an atom or group capable of being displaced by a nucleophile and includes halo (such as chloro, bromo, iodo), alkanesulfonyloxy, arenesulfonyloxy, alkylcarbonyloxy (e.g. acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]-oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in a compound of Formula (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Protecting group" refers to a grouping of atoms that when attached to a reactive group in a molecule masks, reduces or prevents that reactivity. Examples of protecting groups can be found in T. W. Greene and P. G. Futs, *Protective Groups in Organic Chemistry*, (Wiley, 2nd ed. 1991) and Harrison and Harrison et al., *Compendium of Synthetic Organic Methods*, Vols. 1–8 (John Wiley and Sons. 1971–1996). Representative amino protecting groups include formyl, acetyl, trifluoroacetyl, benzyl, benzyloxy-carbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Compounds

In one aspect, the present invention provides compounds represented by the formula:

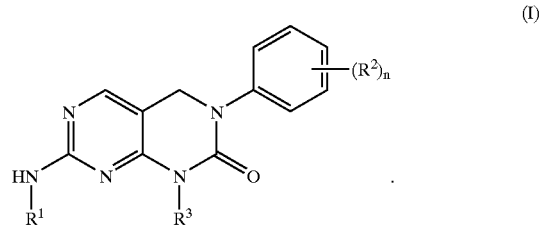

(I)

In formula (I), the symbol $R^1$ represents a hydrogen, alkyl, alkenyl, alkynyl, alkylcarbonyl, cycloalkyl, cycloalkenyl, cycloalkylalkyl, cycloalkylalkenyl, cycloalkylalkynyl, or aralkyl group.

In preferred embodiments, $R^1$ is alkyl, cycloalkyl, or aralkyl, more preferably alkyl or cycloalkyl. In certain preferred embodiments, $R^1$ is a branched alkyl group in which the carbon atom attached to the nitrogen atom is a tetrahedral carbon atom, preferably having 0 or 1 attached hydrogen atoms. For example, $R^1$ will preferably be 2-methyl-2-propyl, 2-propyl, cyclohexyl, 1-methylcyclohexyl, and the like.

Returning to formula I, the symbol $R^2$ represents alkyl, halo, heteroalkyl or vinyl and can be attached to the phenyl ring at any of the remaining five valences otherwise occupied by hydrogen. The subscript n is an integer of from 0 to 3, indicating that the phenyl ring is substituted by from zero to three $R^2$ groups. For those embodiments in which two or three $R^2$ groups are present, each can be independent of the other(s). In preferred embodiments, n is 1 or 2 and each $R^2$ is halo or alkyl, more preferably halo. Still further preferred are those embodiments in which —$(R^2)_n$ represents 2-halo or 2,6-dihalo, more preferably 2-chloro or 2,6-dichloro.

The symbol $R^3$ represents heteroalkyl, heteroalkenyl, heteroalkynyl, heteroalkylcarbonyl, heterosubstituted cycloalkyl, heterosubstituted cycloalkylalkyl, heterosubstituted cycloalkylalkenyl, heterosubstituted cycloalkylalkynyl, heteroalkylsubstituted cycloalkyl, heterocyclyl, heterocyclylalkyl, arylheteroalkyl, heteroarylheteroalkyl, -(alkylene)-C(O)$R^{31}$ or -(heteroalkylene)-C(O)$R^{31}$; wherein $R^{31}$ represents alkyl, haloalkyl, hydroxy, alkoxy, amino, monsubstituted amino, disubstituted amino, cycloalkyl, cycloalkylalkyl, aryl, aralkyl, heteroaryl or heteroaralkyl.

In preferred embodiments, $R^3$ is selected from heteroalkyl, heterocyclyl and heterosubstituted cycloalkyl. In one group of particularly preferred embodiments, $R^3$ is heteroalkyl, more preferably hydroxyalkyl or alkoxyalkyl. Examples of suitable hydroxyalkyl and alkoxyalkyl groups are 2-methoxyethyl, 2-hydroxyethyl, 1-hydroxy-2-propyl, 2-hydroxy-1-propyl, 1-hydroxy-2-(hydroxymethyl)-3-propyl, 1,3-dihydroxy-2-propyl, 1,3-dimethoxy-2-propyl, 1-methoxy-2-(methoxymethyl)-3-propyl, 2,3-dihydroxy-1-propyl, 3,4-dihydroxy-1-cyclopentyl, and the like.

In another group of particularly preferred embodiments, $R^3$ is heterocyclylalkyl. Examples of suitable heterocyclylalkyl groups include 2-(N-piperidinyl)-ethyl, 2-(N-(2-pyrrolidinonyl))ethyl, and the like.

In yet another group of particularly preferred embodiments, $R^3$ is -(alkylene)-C(O)$R^{31}$; wherein $R^{31}$ is hydroxy, amino, methylamino, dimethylamino, methyl, and the like. More preferably the alkylene portion is ethylene or propylene.

In addition to the compounds described above, the present invention includes all pharmaceutically acceptable salts of those compounds along with prodrug forms of the compounds and all isomers whether in a pure chiral form or a racemic mixture or other form of mixture.

Still further, combinations of the preferred groups described above will form other preferred embodiments. For example, in one group of particularly preferred embodiments $R^1$ is alkyl or cycloalkyl, $R^2$ is halo, $R^3$ is heteroalkyl or -(alkylene)-C(O)$R^{31}$; and n is 1 or 2.

Processes for Preparing the Compounds

The compounds of the present invention can be prepared by a variety of methods, using procedures well-known to those of skill in the art. For example, in one embodiment, the compounds are prepared using methods similar to those provided in co-pending U.S. S No. 60/160,804, filed Oct. 21, 1999, and U.S. S No. 60/213,718, filed Jun. 22, 2000 (Bicyclic Nitrogen Heterocycles, and U.S. S Nos. 60/160, 803, and 60/213,743, filed Jun. 22, 2000 (Heteroalkylamino-Substituted Bicyclic Nitrogen Heterocycles) filed Oct. 21, 1999 and outlined in Scheme 1.

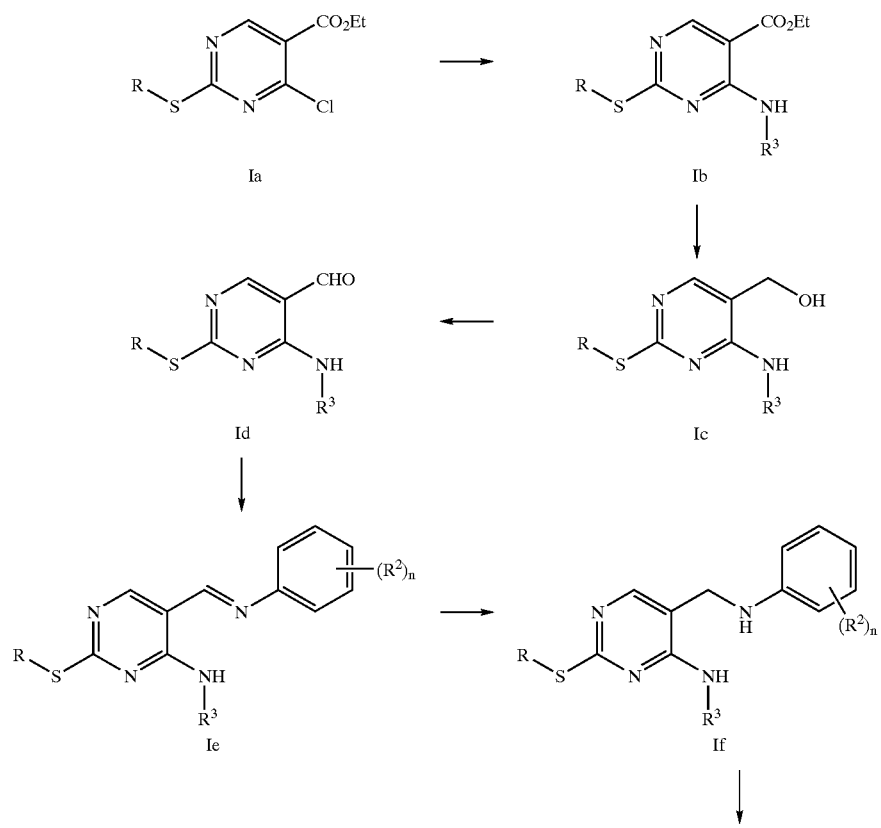

Scheme 1

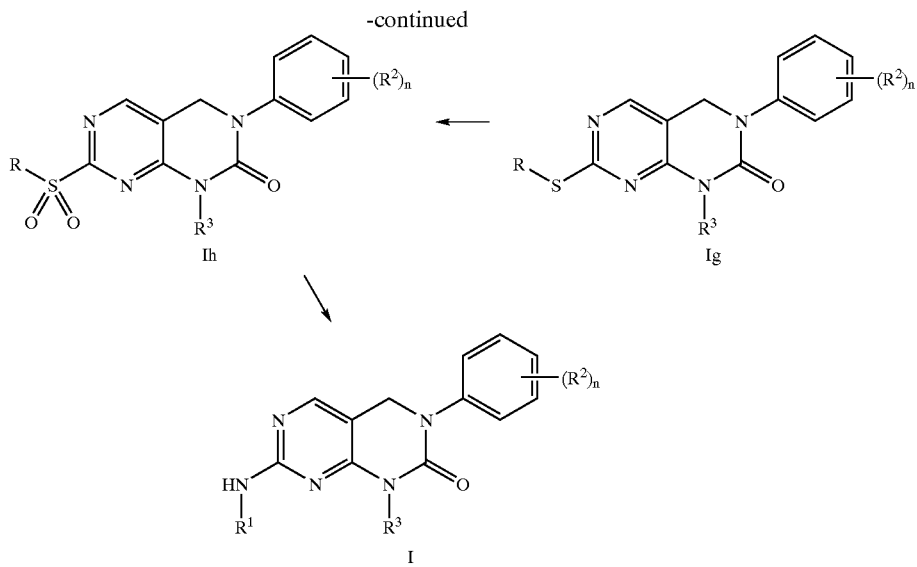

Treatment of a compound of formula Ia with a primary amine ($R^3$—$NH_2$) provides a compound of formula Ib. This reaction is conveniently carried out in a solvent which is inert under the reaction conditions, preferably an open-chain or cyclic ether (such as tetrahydrofuran), a halogenated aliphatic hydrocarbon, especially dichloromethane, an optionally halogenated aromatic hydrocarbon, a formamide or a lower alkanol. Suitably, the reaction is carried out at about −20° C. to about 120° C.

Reduction of a compound of formula Ib provides an alcohol of formula Ic. This reduction is typically carried out using lithium aluminium hydride in a manner well known to those of skill in the art (e.g. in a solvent which is inert under the conditions of the reduction, preferably an open-chain or cyclic ether, especially tetrahydrofuran, at about −20° C. to about 70° C., preferably at about 0° C. to about room temperature).

Oxidation of an alcohol of formula Ic in the next step provides a carboxaldehyde of formula Id. The oxidation is typically carried out with manganese dioxide, although numerous other methods can also be employed (see, for example, Advanced Organic Chemistry, 4$^{th}$ Ed., March, John Wiley & Sons, New York (1992)). Depending on the oxidating agent employed, the reaction is carried out conveniently in a solvent which is inert under the specific oxidation conditions, preferably a halogenated aliphatic hydrocarbon, especially dichloromethane, or an optionally-halogenated aromatic hydrocarbon. Suitably, the oxidation is carried out at about 0° C. to about 60° C.

Reaction of a carboxaldehyde of formula Id with a substituted aniline to provide a compound of formula Ie. This reaction may be carried out in the presence of an acid, e.g. an aromatic sulfonic acid, preferably 4-toluenesulfonic acid, with azeotropic removal of the water formed during the reaction. Conveniently, the reaction is carried out in a solvent which is inert under the reaction conditions, preferably an aromatic hydrocarbon, especially toluene, or an optionally halogenated aromatic hydrocarbon, and at a temperature of about 70° C. to about 150° C., especially at the reflux temperature of the solvent to assist in the noted azeotropic removal of water.

Reduction of a compound of formula Ie to give a compound of formula If can be carried out using, for example, sodium borohydride, lithium aluminium hydride or sodium triacetoxyborohydride under conditions well known to those of skill in the art. Preferably, the compound of formula Ie is not purified, but rather the reaction mixture in which it is prepared is concentrated and the concentrate obtained is taken up in a solvent which is inert under the conditions of the reduction, preferably an open-chain or cyclic ether, especially tetrahydrofuran or an optionally halogenated aromatic hydrocarbon or a lower alkanol, and then treated with an aforementioned reducing agents. The reduction is suitably carried out at about 0° C. to about 100° C., preferably at about 0–25° C.

Cyclization of a compound of formula If provides a bicyclic nitrogen heterocycle of formula Ig. The cyclization can be effected by reaction of If with phosgene or trichloromethyl chloroformate (or phosgene equivalent), conveniently in the presence of a tertiary organic base, preferably a tri(lower alkyl)amine, especially triethylamine. More particularly, the cyclization is carried out in a solvent which is inert under the conditions of the reaction, preferably an open-chain or cyclic ether, especially tetrahydrofuran, an optionally halogenated aromatic hydrocarbon or a halogenated aliphatic hydrocarbon. Conveniently, the reaction is carried out at about −20° C. to about 50° C., preferably at about 0° C. to about room temperature.

Oxidation of Ig with 3-chloroperbenzoic acid provides a sulfone (Ih) which can be converted to a variety of target compounds. Typically the oxidation of Ig is carried out in a solvent which is inert under the conditions of the oxidation, preferably a halogenated aliphatic hydrocarbon, especially chloroform or dichloromethane, and at about −20° C. to about 50° C., preferably about 0° C. to about room temperature.

Finally, treatment of Ih with an amine ($R^1$—$NH_2$) provides the target compounds of formula I. The reaction can be carried out in the presence or absence of solvent. Conveniently, the reaction is carried out at temperatures of from about 0° C. to about 200° C., more preferably about room temperature to about 150° C.

Accordingly, the present invention provides a method of preparing compounds of formula I, by treating a compound of general formula Ii with an amine ($R^1$—$NH_2$).

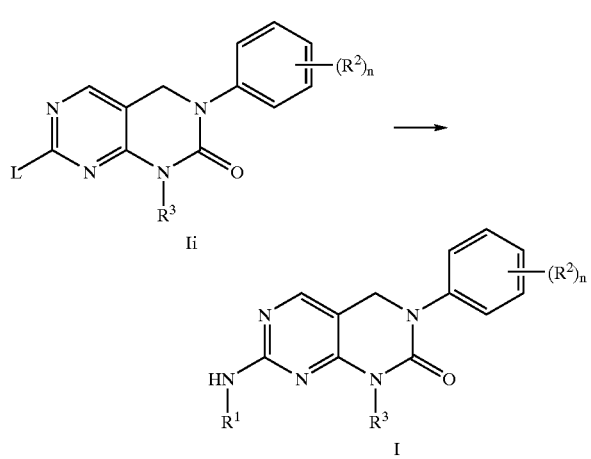

In compound Ii, the symbols $R^2$, $R^3$ and the subscript n have the meanings provided above with reference to formula I. The letter L represents a leaving group which can be a halogen, a lower alkanesulfonyl group (e.g., methanesulfonyl or trifluoromethanesulfonyl) or an aromatic sulfonyl group (e.g., benzenesulfonyl or 4-toluenesulfonyl). Other suitable leaving groups are known to those of skill in the art and can be found in, for example, Advanced Organic Chemistry, 4$^{th}$ Ed., March; John Wiley & Sons, New York (1992). Suitable amines ($R^1$—$NH_2$) are those in which $R^1$ represents any of the $R^1$ groups noted for formula I.

In a preferred embodiment, the bicyclic nitrogen heterocycle can be constructed and $R^3$ can be introduced at a later stage of synthesis as shown in Scheme 2.

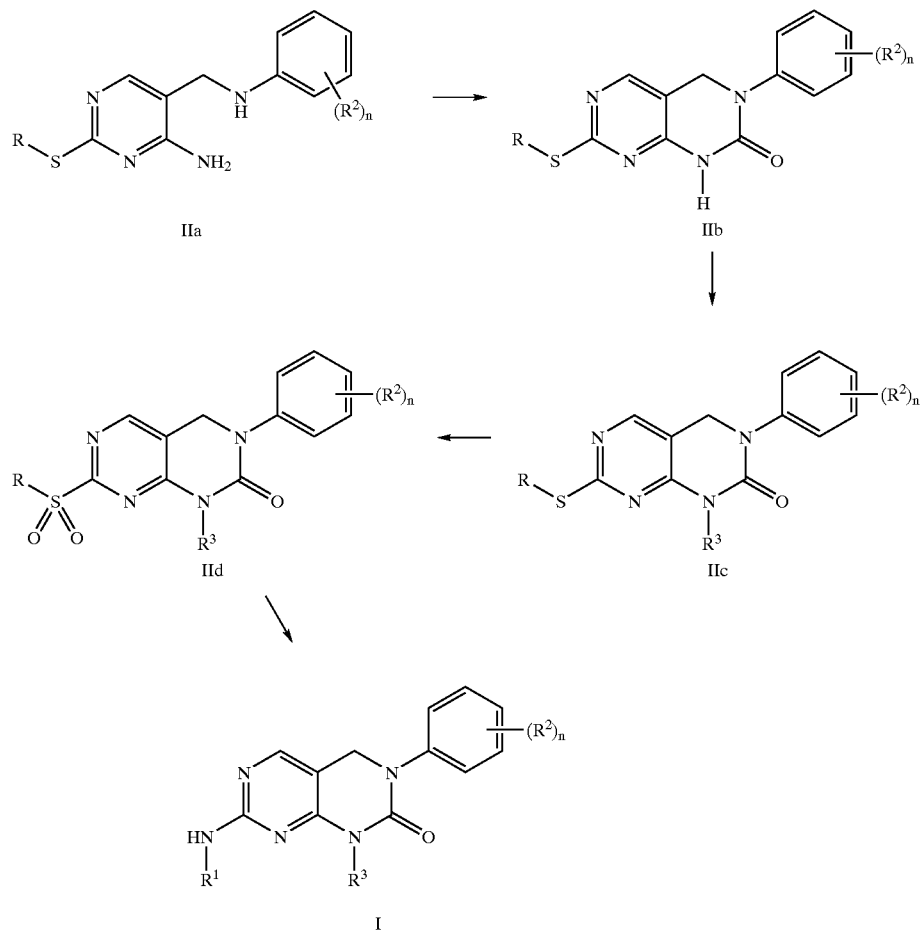

Compound IIa, the starting material in Scheme 2, can be prepared from commercially available ethyl 4-amino-2-mercapto-pyrimidine-5-carboxylate. Briefly, treatment of the mercapto compound with a suitable alkylating agent (R—X) provides a compound of formula Ib ($R^3$=H). Conversion of Ib ($R^3$=H) to IIa can follow the steps provided in Scheme I.

Cyclization of IIa provides a bicyclic nitrogen heterocycle of formula IIb. The cyclization can be effected by reaction of IIa with phosgene or trichloromethyl chloroformate (or phosgene equivalent), typically in the presence of a tertiary organic base, preferably a tri(lower alkyl)amine, especially triethylamine. More particularly, the cyclization is carried out in a solvent which is inert under the conditions of the reaction, preferably an open-chain or cyclic ether, especially tetrahydrofuran, an optionally halogenated aromatic hydrocarbon or a halogenated aliphatic hydrocarbon. Conveniently, the reaction is carried out at about −20° C. to about 50° C., preferably at about 0° C. to about room temperature.

Introduction of an $R^3$ group to provide a compound of formula IIc can be accomplished under a variety of conditions. For example, IIb can be treated with alkali metal hydride, especially sodium hydride, and subsequent reaction with a compound of the general formula $R^3$—L, wherein $R^3$ has any of the values accorded to $R^3$ hereinbefore except hydrogen, aryl or heteroaryl and L represents a leaving group (e.g., halo, methanesulfonate, toluenesulfonate, trifluoromethanesulfonate, and the like). The N-substitution is conveniently carried out in a solvent which is inert under the reaction conditions, preferably a formamide, especially N-methylpyrrolidinone or dimethylformamide, an open-chain or cyclic ether or an optionally halogenated aromatic hydrocarbon. Suitably, the reaction is carried out at about 50° C. to about 200° C., preferably at about 50° C. to about 150° C. Alternatively, the alkylation may be carried out with an inorganic base such as potassium carbonate in a formamide solvent such as N-methylpyrrolidinone temperatures from about 0° C. to about 25° C.

An alternative, and preferable method for the introduction of $R^3$ involves alkylation of the pyrimidinone nitrogen under Mitsonobu conditions. In this method, an alcohol of the general formula $R^3$—OH is combined with a compound of general formula IIb in the presence of, for example, triphenylphosphine and diethyl azodicarboxylate or diphenylpyridyl phosphine and t-butylazodicarboxylate (See, *Tetrahedron Lett.*, 40: 4497–4500 (1999). The alkylation is conveniently carried out in a solvent which is inert under the reaction conditions, preferably an open-chain or cyclic ether, at temperatures of about −20° C. to about 100° C., preferably at about 0° C. to about 30° C. (or room temperature). As with other alkylation methods, primary and secondary alcohols are the most suitable for reaction under these conditions.

Following the introduction of $R^3$, the oxidation and displacement steps (to introduce $R^1$—NH—) can be accomplished as outlined above to provide target compounds of formula I.

In alternate routes, IIb may be converted to IId by first alkylating IIb under Mitsunobu conditions to introduce $R^3$, followed by oxidation of the sulfide to the corresponding sulfone IId.

In still other embodiments, the compounds can be prepared by reversing the order of alkylation and displacement steps, thereby reversing the order of —$R^3$ and —NH—$R^1$ introduction, shown in Scheme 3.

Scheme 3

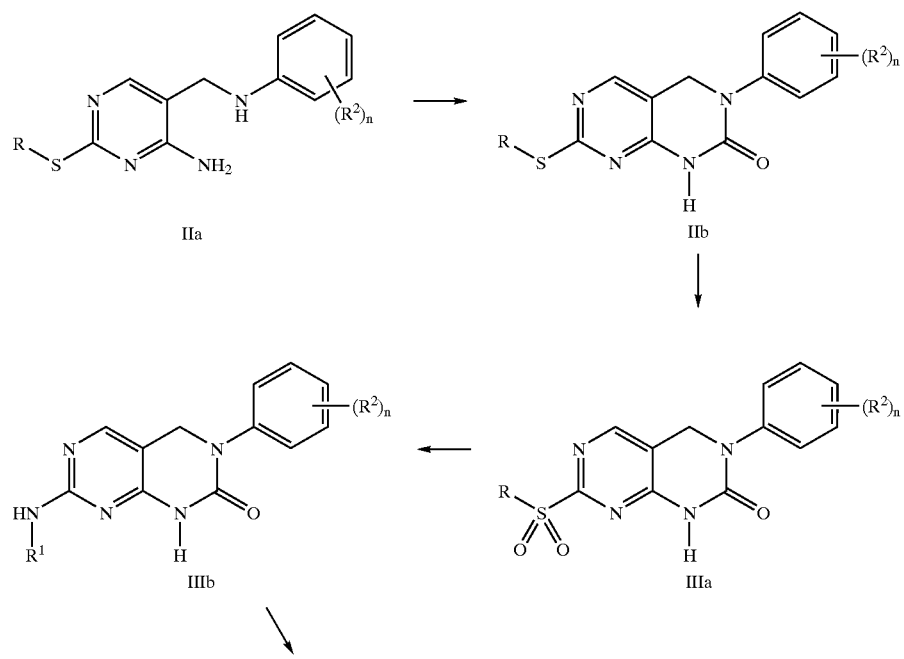

-continued

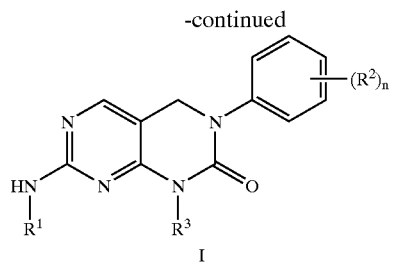

I

Accordingly, a compound of formula IIa can be cyclized to IIb (as initially shown in Scheme 2). Oxidation of IIb to IIIa provides the template for the subsequent displacement and alkylation steps. Thus, treatment of IIIa with $R^1$—$NH_2$ under the conditions described above, provides IIIb, which can be alkylated using $R^3$—L (wherein L has the meaning noted above) or $R^3$—OH under Mitsunobu conditions to provide the target compounds of formula I.

One of skill in the art will understand that certain modifications to the above schemes are contemplated and within the scope of the present invention. For example, certain steps will involve the protection and deprotection of reactive functional groups that are not compatible with particular reaction conditions.

Pharmaceutical Compositions Containing the Compounds

The compounds of formula I and the pharmaceutically acceptable salts of basic compounds of formula I with acids can be used as medicaments, e.g. in the form of pharmaceutical preparations. The pharmaceutical preparations can be administered enterally, e.g. orally in the form of tablets, coated tablets, dragées, hard and soft gelatine capsules, solutions, emulsions or suspensions, nasally, e.g. in the form of nasal sprays, or rectally, e.g. in the form of suppositories. However, they may also be administered parenterally, e.g. in the form of injection solutions.

The compounds of formula I and their aforementioned pharmaceutically acceptable salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain therapeutically valuable substances other than the compounds of formula I and their aforementioned pharmaceutically acceptable salts.

Medicaments which contain a compound of formula I or a pharmaceutically acceptable salt of a basic compound of formula I with an acid in association with a compatible pharmaceutical carrier material are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of formula I and their aforementioned pharmaceutically acceptable salts can be used in accordance with the invention as therapeutically active substances, especially as antiinflammatory agents or for the prevention of graft rejection following transplant surgery. The dosage can vary within wide limits and will, of course, be fitted to the individual requirements in each particular case. In general, in the case of administration to adults a convenient daily dosage should be about 0.1 mg/kg to about 100 mg/kg, preferably about 0.5 mg/kg to about 5 mg/kg. The daily dosage may be administered as a single dose or in divided doses and, in addition, the upper dosage limit referred to earlier may be exceeded when this is found to be indicated.

Finally, the use of compounds of formula I and their aforementioned pharmaceutically acceptable salts for the production of medicaments, especially in the treatment or prophylaxis of inflammatory, immunological, oncological, bronchopulmonary, dermatological and cardiovascular disorders, in the treatment of asthma, central nervous system disorders or diabetic complications or for the prevention of graft rejection following transplant surgery, is also an object of the invention.

Methods of Using the Compounds and Compositions

Compounds of formula I would be useful for, but not limited to, the treatment of any disorder or disease state in a human, or other mammal, which is excacerbated or caused by excessive or unregulated TNF and/or IL-1 or p38 kinase production by such mammal. Accordingly, the present invention provides a method of treating a cytokine-mediated disease which comprises administering an effective cytokine-interfering amount of a compound of formula I, or a pharmaceutically acceptable salt or tautomer thereof.

Compounds of formula I would be useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpesvirus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of influenza, multiple sclerosis, cancer, diabetes, systemic lupus erthrematosis (SLE), skin-related conditions such as psoriasis, eczema, burns, dermatitis, keloid formation, and scar tissue formation. Compounds of the invention also would be useful to treat gastrointestinal conditions such as inflammatory bowel disease, Crohn's disease, gastritis, irritable bowel syndrome and ulcerative colitis. The compounds would also be useful in the treatment of ophthalmic diseases, such as retinitis, retinopathies, uveitis, ocular photophobia, and of acute injury to the eye tissue. Compounds of the invention also would be useful for treatment of angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemaginomas, including invantile hemaginomas, angiofibroma of the nasopharynx and avascular necrosis of bone; diabetic nephropathy and cardiomyopathy; and disorders of the female reproductive system such as endometriosis. The compounds of the invention may also be useful for preventing the production of cyclooxygenase-2 and the compounds of this invention are also expected to be useful in the prevention and treatment of cancer, in particular colon cancer. The compounds of this invention are also expected to be useful in the prevention and treatment of Alzheimer's disease.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

The following examples are offered to illustrate, but not to limit the claimed invention.

In the examples below, unless otherwise stated, temperatures are given in degrees Celsius (° C.); operations were carried out at room or ambient temperature (typically a range of from about 18–25° C.; evaporation of solvent was carried out using a rotary evaporator under reduced pressure (typically, 4.5–30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours)

DEAD stands for diethyl azodicarboxylate

DIAD stands -for. diisopropyl azodicarboxylate

Example 1

This example illustrates the preparation of 3-(2-chlorophenyl)-1-ethoxy-carbonylmethyl-7-isopropylamino-3,4-dihydropyrimido[4,5-d]pyrimidin-2(1H)-one and 3-(2-chloro-phenyl)-1-carboxymethyl-7-isopropylamino-3,4-dihydropyrimido[4,5-d]-pyrimidin-2(1H)-one beginning with 7-benzylthio-3-(2-chlorophenyl)-3,4-dihydropyrimido-[4,5-d]pyrimidin-2(1H)-one.

1.1 Alkylation of Pyrimidinone

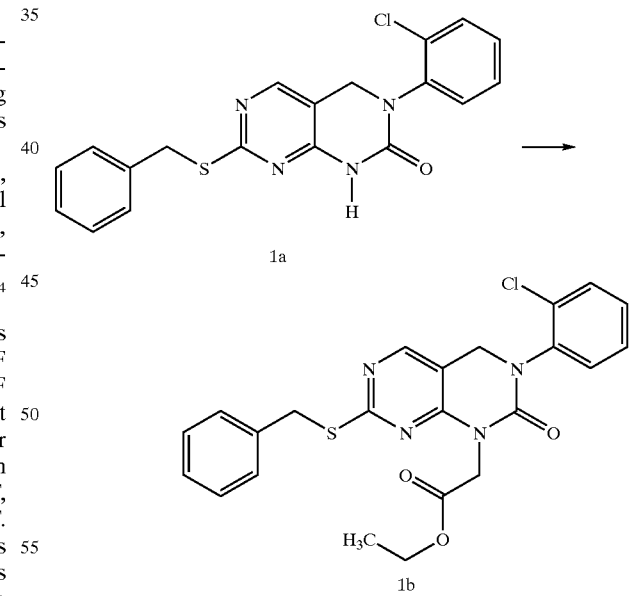

Sulfide 1a, 7-benzylthio-3-(2-chlorophenyl)-3,4-dihydropyrimido[4,5-d]-pyrimidin-2(1H)-one, (1.5 g, 3.92 mmole, prepared as described in Example 6) was dissolved in dimethylformamide (15 mL) and sodium hydride (60%, 0.172 g, 4.31 mmole) was added. The resulting mixture was stirred for twenty minutes, then ethyl bromoacetate (0.87 mL, 7.84 mmole) was added. After 3 hours, the reaction was quenched with water and extracted three times with ethyl acetate. The combined extracts were washed five times with water, dried over MgSO₄, and concentrated in vacuo. The residue was purified with column chromatography on silica gel using 30:70 acetone/hexane to give 1.283 g of ester 1b.

1.2 Oxidation of benzyl sulfide

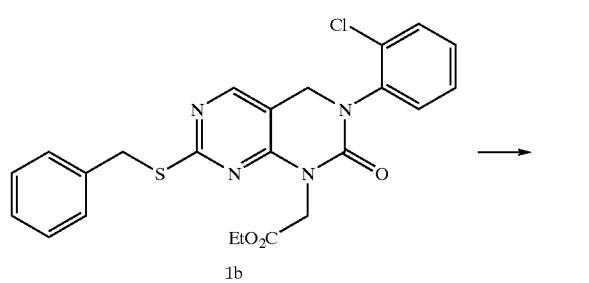

1b

Ester 1b (0.600 g, 1.28 mmole) was dissolved in chloroform (15 mL) and 3-chloroperoxybenzoic acid (50%, 0.883 g, 2.56 mmole) was added at room temperature. The mixture was stirred for 2 hours, then washed three times with 10% (w/w) aqueous sodium sulfite, once with saturated aqueous sodium bicarbonate, and once with water. The organic layer was dried over MgSO₄ and concentrated in vacuo to provide 0.670 g of benzyl sulfone 1c.

1.3 Displacement of sulfone

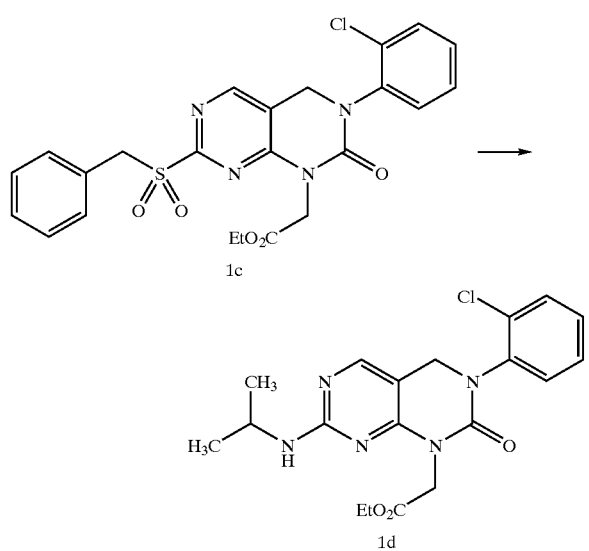

1c

1d

Benzyl sulfone 1c (0.520 g, 1.04 mmole) and isopropylamine (0.18 mL, 2.08 mmole) were combined and heated to 90–100° C. for one hour. The reaction was cooled to room temperature and the mixture was purified by column chromatography on silica gel using 18:1 CH₂Cl₂/MeOH. Fractions containing the product were combined and concentrated to provide 0.366 g of 1d, 3-(2-chloro-phenyl)-1-ethoxycarbonylmethyl-7-isopropylamino-3,4-dihydropyrimido[4,5-d]pyrimidin-2(1H)-one (mass spec. MH⁺=404. Mpt.188.8–191.4° C.).

1.4 Saponification of Ethyl ester

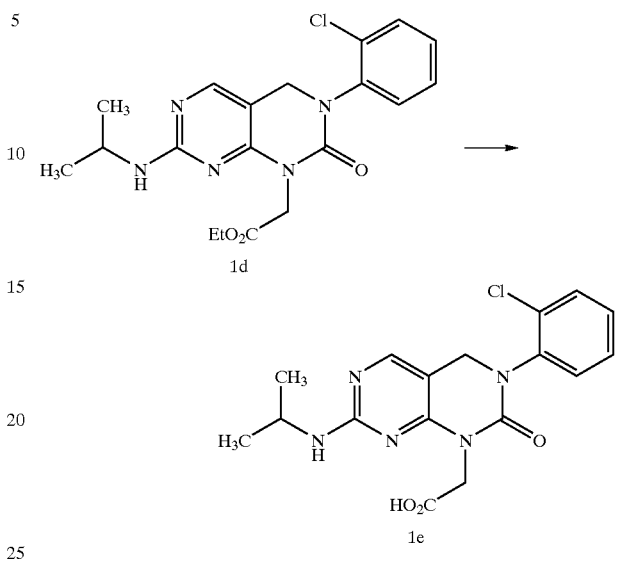

1d

1e

To a solution of 1d (0.266 g, 0.66 mmol) in MeOH (10 mL) was added sodium hydroxide (0.026 g, 0.66 mmol) and water (3 mL). The reaction mixture was stirred at room temperature for 12 hours. The mixture was concentrated in vacuo and triturated in ethyl acetate, then redissolved in MeOH and concentrated in vacuo. The residue was triturated in ether, filtered and dried to give 0.225 g of 1e, 3-(2-chloro-phenyl)-1-carboxymethyl-7-isopropylamino-3,4-dihydropyrimido[4,5-d]pyrimidin-2(1H)-one (mass spec. MH⁺=376, mpt. 172.0–188.0° C.

Example 2

This example illustrates the preparation of 3-(2-chloro-phenyl)-1-(2-methoxy-ethyl)-7-isopropylamino-3,4-dihydropyrimido[4,5-d]pyrimidin-2(1H)-one, in which an alkylation is carried out using Mitsunobu conditions.

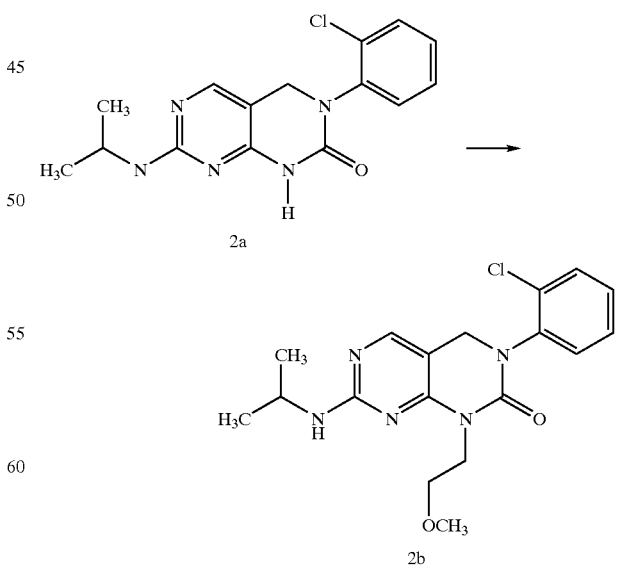

2a

2b

To a solution of pyrimidinone 2a (0.500 g, 1.57 mmol, prepared by treatment of 7-benzylsulfonyl-3-(2-chlorophenyl)-3,4-dihydropyrimido[4,5-d]pyrimidin-2(1H)-one with isopropylamine under conditions as in 1.3 above) in THF (20 mL) was added triphenyl phosphine (0.413 g, 1.57 mol) and 2-methoxyethanol (0.12 mL, 1.57 mmol). The mixture was cooled to 0° C. and DIAD (0.31 mL, 1.57 mmol) was added. The reaction was allowed to warm to room temperature and stirred for 12 hr. Additional portions of 2-methoxyethanol (0.12 mL, 1.57 mmol), triphenylphosphine (0.413 g, 1.57 mmol) and DIAD (0.31 mL, 1.57 mmol) were added and the mixture was stirred for another 12 hours at room temperature, then heated to 55–60° C. After 2 hr, the mixture was concentrated in vacuo and the residue was purified by column chromatography on silica gel using 1:1 hexane/ethyl acetate as eluant. The fractions containing product were combined and concentrated to an oil which was redissolved in ethyl acetate. Hydrochloric acid (1.0M/Et$_2$O, 0.6 mL) was added to provide the salt. The mixture was stirred for 12 hours then concentrated in vacuo. The residue was triturated in ether over dry ice and slowly allowed to warm to room temperature as the mixture stirred for 12 hours. The solid was filtered to give 0.139 g of the hydrochloride salt of the title compound, 2b (mass spec. MH$^+$=376, mpt. 126.0–131.6° C.).).

Example 3

This example illustrates the preparation of 3-(2-chlorophenyl)-7-isopropylamino-1-(2-methylsulfonylethyl)-3,4-dihydropyrimido[4,5-d]pyrimidin-2(1H)-one.

3.1 "Mitsunobu" Alkylation of Pyrimidinone

Benzyl sulfide 1a (500 mg, 1.31 mmol) was taken up in 2 mL THF with 2-(methylthio)ethanol (114 μl, 1.31 mmol), triphenylphosphine (343 mg, 1.31 mmol), and DEAD (0.21 mL, 1.31 mmol). The mixture was stirred at room temperature for 4 days, evaporated in vacuo, and purified by chromatography on silica gel with 5–20% acetone/hexanes as eluant, to provide 3a (529 mg, 1.16 mmol, 88%).

3.2 Oxidation of benzyl sulfide

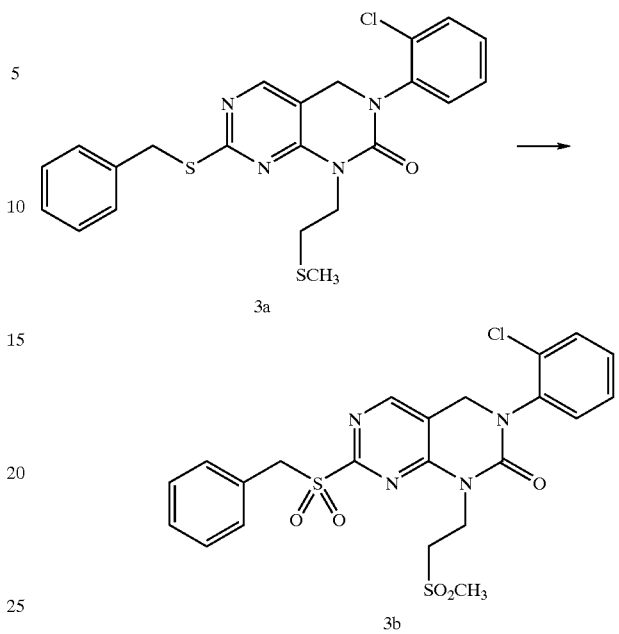

Oxidation of 3a was accomplished using m-CPBA (1.19 g, 5.8 mmol) in CH$_2$Cl$_2$ with stirring at room temperature for 5 hours. The reaction was quenched with 10% Na$_2$SO$_3$ (aq, 50 mL) and extracted three times with CH$_2$Cl$_2$. The combined extracts were washed with sat. NaHCO$_3$ and concentrated in vacuo to provide 3b, which was used without purification.

3.3 Displacement of sulfone

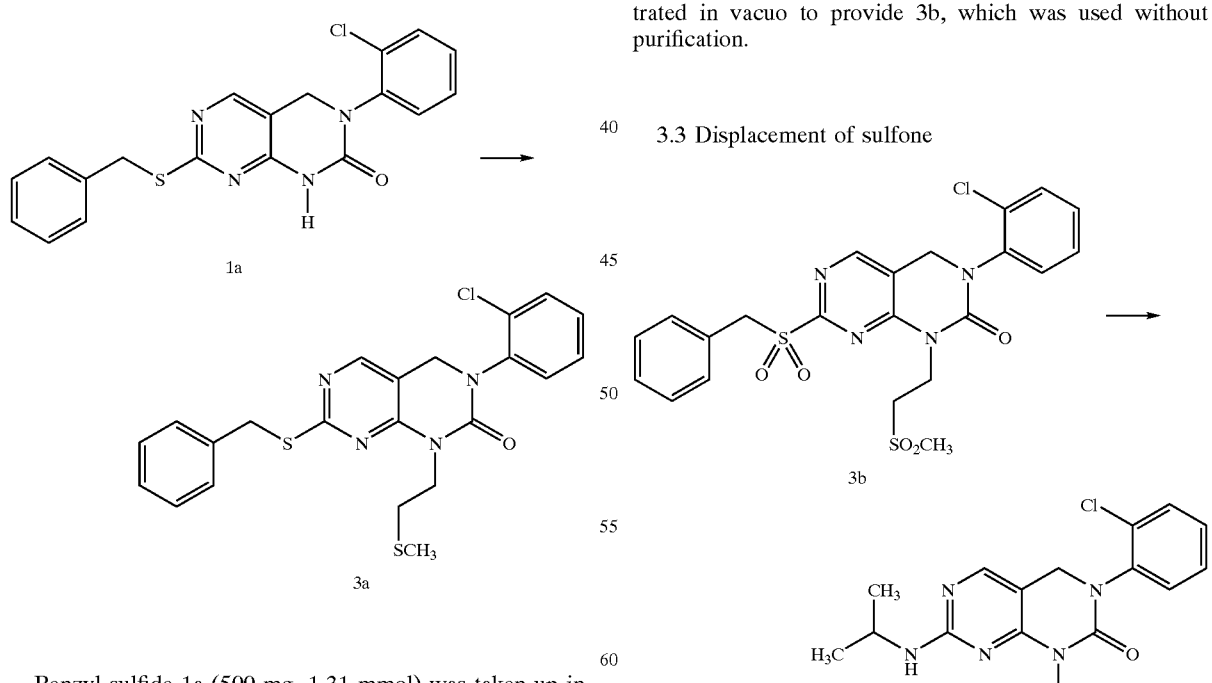

The crude product 3b was taken up in isopropylamine (5 mL, 58 mmol) and stirred neat at room temperature for 2 days. The mixture was concentrated in vacuo and purified by chromatography on silica gel using 10–50% acetone/hexanes as eluant to provide 3c (287 mg, 0.732 mmol, 63% from 3a, 56% from 1a). The purified product was taken up in ethyl acetate and treated with 1 equivalent HCl/Et$_2$O to precipitate the HCl salt of 3c. (mass spec. MH$^+$=424)

Example 4

This example illustrates the preparation of 3-(2-chlorophenyl)-1-(2-hydroxyethyl)-7-isopropylamino-3,4-dihydropyrimido[4,5-d]pyrimidin-2(1H)-one.

4.1 "Mitsunobu" Alkylation of Pyrimidinone

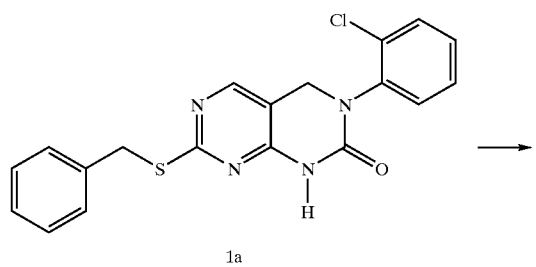

1a

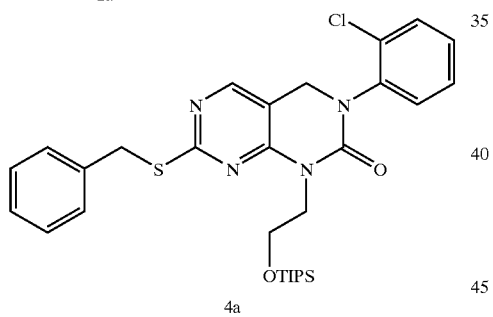

4a

Benzyl sulfide 1a (500 mg, 1.31 mmol) was taken up in 7 mL DMF and treated with tri-isopropylsilyl protected iodoethanol (555 mg, 1.57 mmol, prepared according to the procedures described in *J. Am. Chem. Soc.,* 112(10), 4078–9 (1990) and *J.Chem. Soc. Perkin Trans.,* 1(6), 1417–23, (1998)) and chilled to 0° C. Sodium hydride (60% in oil, 63 mg, 1.57 mmol) was added and the reaction mixture was warmed from 0° C. to 30° C. then stirred overnight at 30° C. An additional 63 mg of 60% sodium hydride was added. After another 6 hours, the reaction was quenched by additon of 10 mL of water. The resulting mixture was extracted with EtOAc and CH$_2$Cl$_2$, and the combined extracts were dried over MgSO$_4$, concentrated in vacuo, and purified by chromatography on silica gel using 10–20% acetone/hexanes as eluant to provide 4a (430 mg, 0.738 mmol, 56%).

4.2 Oxidation of benzyl sulfide

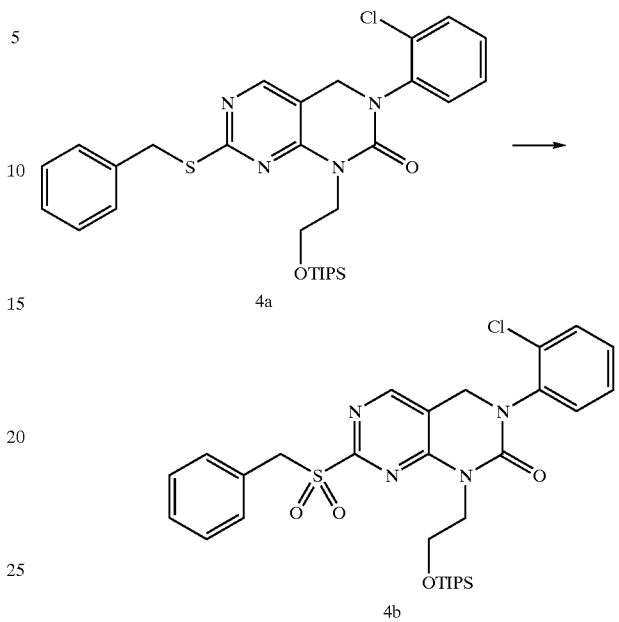

Oxidation of 4a was accomplished with m-CPBA (500 mg, 2.46 mmol) in CH$_2$Cl$_2$. After quenching the reaction with Na$_2$SO$_3$(aq), the crude product 4b was extracted with CH$_2$Cl$_2$, washed with sat. NaHCO$_3$, concentrated in vacuo, and used without purification.

4.3 Displacement of sulfone

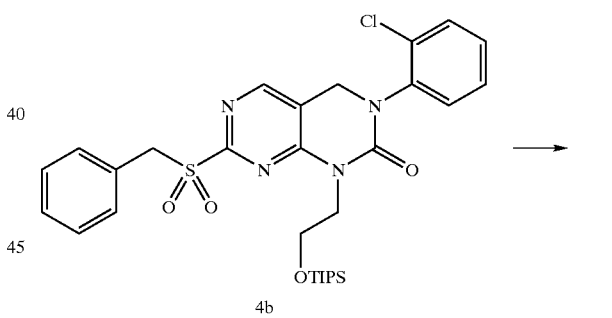

4b

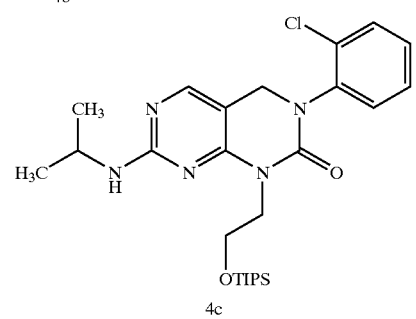

4c

The crude benzyl sulfone 4b was taken up in 3 mL CH$_2$Cl$_2$ containing isopropylamine (1 mL, 11.7 mmol), stirred at 80° C. overnight, concentrated in vacuo, and purified by chromatography on silica gel with 5–20% acetone/hexanes as eluant, to provide 4c (281 mg, 0.542 mmol, 73% from 4a).

4.4 Deprotection of hydroxy group

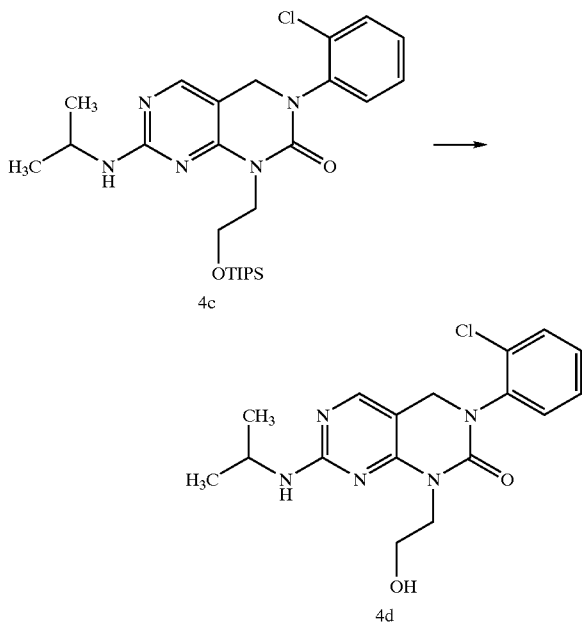

Deprotection of 4c was accomplished with tetrabutylammonium fluoride (0.54 mL 1M/THF, 0.542 mmol) in THF, with stirring at room temperature for 4 hours. The mixture was evaporated in vacuo and purified using chromatography on silica gel with 10–40% acetone/hexanes as eluant, to provide 4d (179 mg, 0.495 mmol). The purified product was taken up in ethyl acetate and treated with 1 equivalent HCl/Et$_2$O to precipitate out the HCl salt of 4d. (mass spec. MH$^+$=362)

Example 5

This example illustrates the preparation of 4-amino-2-benzylthiopyrimidine-5-carboxaldehyde.

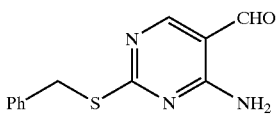

a) 272 g (4.0 mol) of sodium ethoxide (Lancaster) was stirred in 1 L of ethanol and treated with 304 g (4.0 mol) thiourea (Avocado). 676 g (4.0 mol) of ethyl ethoxymethylene cyanoacetate (Avocado) was added and the mixture heated at reflux for 8 hours. After cooling to room temperature overnight, the reaction mixture was treated sequentially with 2 L of water and 400 mL of acetic acid. The reaction mixture was heated at reflux for 30 minutes, cooled to room temperature, and the suspension filtered. The solid was washed three 500 mL portions of water, two 500 mL portions of acetone, and 500 mL of diethyl ether. The product was dried to give 473.3 g (60%) of 4-amino-5-carbethoxy-pyrimidine-2-thiol as a cream solid of melting point >250° C.
b) A stirred suspension of 473 g (2.377 mol) of 4-amino-5-carbethoxy-pyrimidine-2-thiol in 3.5 L of ethanol was treated with 180.4 g (1.307 mol) of potassium carbonate and 447.1 g (2.615 mol) of benzyl bromide. The mixture was heated at reflux for 2 hours then allowed to cool to room temperature overnight. The suspension was filtered and the solid washed with two 500 mL portions of ethanol, 2 L of water and two 500 mL portions of water. The product was dried in vacuo over phosphorus pentoxide at 50° C. to give 416 g (61%) of ethyl 4-amino-2-benzylthiopyrimidine-5-carboxylate as a cream solid of melting point 117–118° C.
c) A solution of 462.4 g (1.6 mol) of ethyl 4-amino-2-benzylthiopyrimidine-5-carboxylate in 2.3 L of sieve-dried tetrahydrofuran was added slowly with stirring to 1.6 L (1.6 mol) of a 1M solution of lithium aluminium hydride in tetrahydrofuran under a nitrogen atmosphere with ice-cooling. The solution was added at a rate to maintain a temperature of 18–20° C. On completion of the addition, the mixture was heated to 60° C. and treated cautiously with 60.8 mL of water during 1.5 hours. 60.8 mL of 15% aqueous sodium hydroxide was added during 30 minutes, followed by 182.5 mL of water during 30 minutes. The suspension was stirred at 60° C. overnight then filtered through Hyflo filter aid while still hot, and the solid washed with two 1 L portions of tetrahydrofuran. Evaporation of the filtrate to dryness gave 392.5 g (99%) of 4-amino-2-benzylthiopyrimidine-5-methanol as an off-white solid which was used in the next step without further purification.
d) A suspension of 392.5 g (1.59 mol) of 4-amino-2-benzylthiopyrimidine-5-methanol in 7.75 L of dichloromethane under a nitrogen atmosphere was treated with 1.382 Kg (15.9 mol) of activated manganese dioxide (Acros). The reaction mixture was stirred at ambient temperature overnight then filtered through Hyflo filter aid. The solid was washed with three 1 L portions of dichloromethane and the combined filtrates evaporated to give 340.5 g (88%) of 4-amino-2-benzylthiopyrimidine-5-carboxaldehyde as a pale yellow solid of melting point 136–139° C.

Example 6

This example illustrates the preparation of 7-benzylthio-3-(2-chlorophenyl)-3,4-dihydropyrimido[4,5-d]pyrimidin-2(1H)-one.

6.1 Preparation of 5-(2-chlorophenyl)aminomethyl-4-amino-2-benzylthiopyrimidine

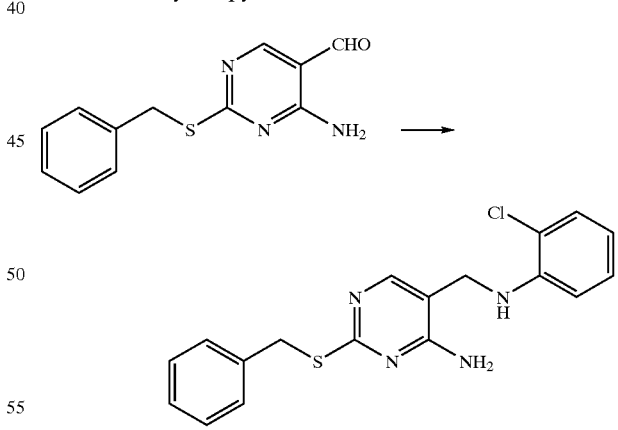

A mixture of 5 g (20.4 mmol) of 4-amino-2-benzylthiopyrimidine-5-carboxaldehyde, 2.25 mL (21.4 mmol) of 2-chloroaniline and 0.1 g (0.5 mmol) of 4-toluenesulfonic acid monohydrate in 60 mL of toluene was heated under reflux with azeotropic removal of water for 3 hours. The mixture was cooled to 0° C. and the precipitate was collected by vacuum filtration and was washed with hexanes and air dried. This solid was then dissolved in 100 mL THF and the reaction cooled to 0° C. Lithium aluminum hydride (0.735 g, 18.8 mmol) was added in small portions over 45 minutes. Once the addition was complete, the mixture was stirred for a further 15 minutes and carefully treated sequentially with 0.8 mL H₂O, 0.8 mL of 15% aq. NaOH and then 2.4 mL of H₂O. The mixture was stirred for 30 minutes, filtered through celite, and the filtrate concentrated in vacuo. The solid was stirred with diethyl ether, filtered and air dried to give 6.1 g of 5-(2-chlorophenyl) aminomethyl-4-amino-2-benzylthiopyrimidine as a white solid.

6.2 Preparation of 3-(2-chlorophenyl)-7-benzylthio-3,4-dihydropyrimido-[4,5d]pyrimidin-2(1H)-one

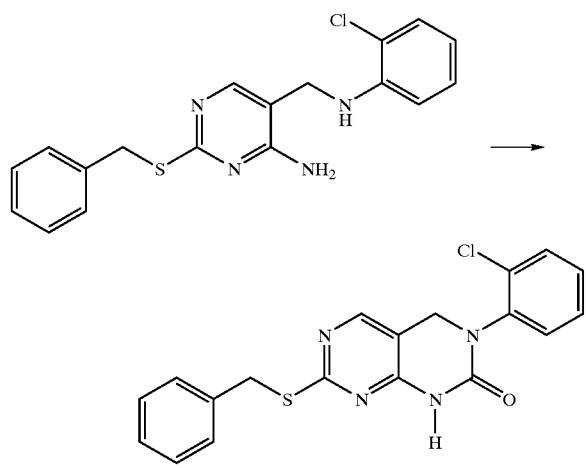

To a stirred solution, cooled to −10° C., of 4.3 g (12.1 mmol) of 5-(2-chlorophenyl) aminomethyl-4-amino-2-benzylthiopyrimidine in 100 mL of tetrahydrofuran was added 3.1 mL (22.2 mmol) of triethylamine. This solution was then treated dropwise with a solution of 6.15 mL of phosgene (20% solution in toluene; 11.8 mmol) After stirring for 30 minutes, an additional 1.0 mL of triethylamine (7.1 mmol) was added followed by 2.0 mL of phosgene (20% solution in toluene; 3.8 mmol). The reaction was warmed to room temperature, treated with 0.5 mL H₂O and stirred for 30 minutes. The reaction was then filtered and the mother liquor was concentrated and stirred with dichloromethane. The product was then collected by vacuum filtration and dried in vacuo to give 3.83 g of 7-benzylthio-3-(2-chlorophenyl)-3,4-dihydropyrimido[4,5-d]-pyrimidin-2(1H)-one as a white solid.

Example 7

This example illustrates the preparation of 7-benzylsulfonyl-3-(2-chlorophenyl)-3,4-dihydropyrimido[4,5-d]pyrimidin-2(1H)-one

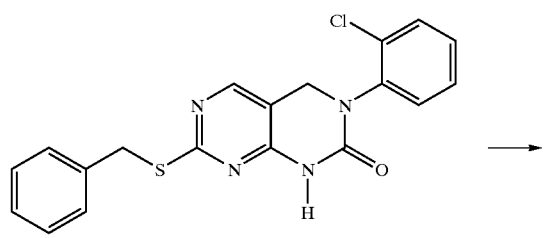

-continued

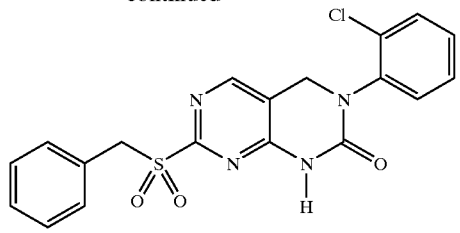

A suspension of 1 g (2.61 mmol) of 7-benzylthio-3-(2-chlorophenyl)-3,4-dihydropyrimido[4,5-d]pyrimidin-2(1H)-one in 10 mL of dichloromethane was cooled in ice and treated with 1.29 g (5.23 mmol) of 70% 3-chloroperbenzoic acid. The mixture was stirred at room temperature for 2 hours, then treated with 25 mL of 10% aq. Na₂S₂O₃ and left to stir for 30 minutes. The reaction was diluted with 100 mL dichloromethane and the phases were separated. The organic phase was washed with 10% aq. K₂CO₃, brine, and then dried over magnesium sulfate and filtered. Concentration of the filtrate under reduced pressure gave 0.73 g of 7-benzylsulfonyl-3-(2-chlorophenyl)-3,4-dihydropyrimido[4,5-d]-pyrimidin-2(1H)-one as a white solid.

Example 8

This example illustrates the preparation of 3-(2-chlorophenyl)-1-[(2S)-2,3-dihydroxyethyl]-7-isopropylamino-3,4-dihydropyrimido[4,5-d]pyrimidin-2(1H)-one Step 1

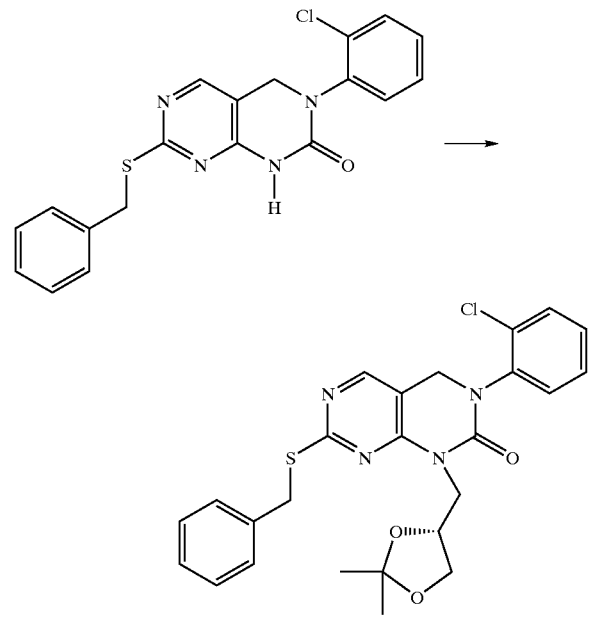

A mixture of 1.0 g (2.6 mmol) of 7-benzylthio-3-(2-chlorophenyl)-3,4-dihydro-pyrimido[4,5-d]pyrimidin-2(1H)-one, 1.5 g (5.2 mmol) L-α,β-isopropylidene glycerol-γ-tosylate and 1.44 g (10.4 mmol) of potassium carbonate was stirred in DMF (20 mL) and heated at 80° C. under nitrogen atmosphere. After 16 hours, the reaction mixture was cooled to room temperature, poured in to a brine solution, extracted with ethyl acetate and dried over sodium sulfate. The solution was concentrated under vacuum, purified by flash chromatography (eluting with 40% EtOAc/Hexane) to give 1.1 g of the isopropylidene ketal adduct as an oil. (mass spec. MH⁺=496).

Step 2

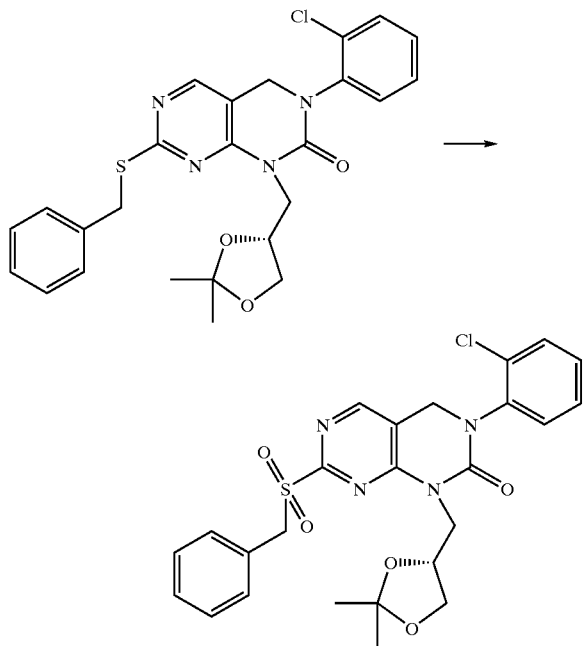

To a solution of 1.2 g (2.4 mmol) of the isopropylidene ketal adduct prepared above, in methylene chloride (25 mL), cooled in a wet ice bath under nitrogen atmosphere, was added 1.8 g (9.6 mmol) of m-chloroperbenzoic acid portionwise. The resulting suspension was stirred and allowed to warm to room temperature. After 16 hours, the reaction mixture was cooled in a wet ice bath and a 10% aqueous solution of sodium bisulfite (50 mL) was added dropwise. The mixture was stirred for 30 minutes and the layers were separated. The aqueous layer was extracted with methylene chloride and the combined organic fractions were washed with brine, dried over sodium sulfate and concentrated to dryness. The residue was purified by flash chromatography (gradient elution: 60–100% ethyl acetate/hexane). The sulfone product was isolated (0.73 g) as a foam. (mass spec. MH⁺=529).

Step 3

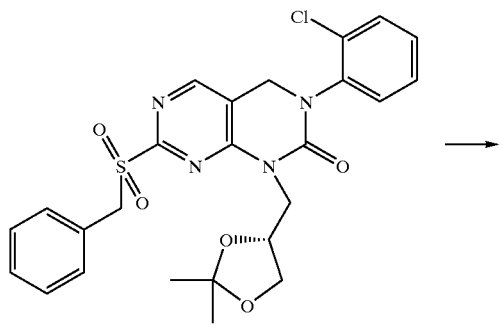

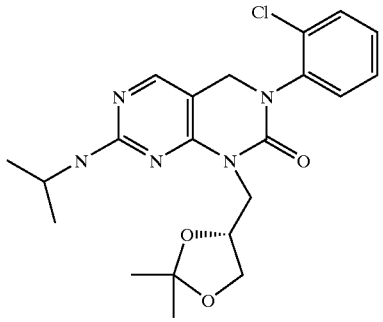

A solution of 0.7 g (1.3 mmol) of the sulfone prepared above in 10 mL of isopropylamine was heated at 40° under nitrogen atmosphere. After 3 hours, the reaction mixture was cooled to room temperature, concentrated to dryness and purified by flash chromatography (elution with 60% ethyl acetate/hexane) to give 0.42 g of the isopropyl amine adduct as a foam.

Step 4

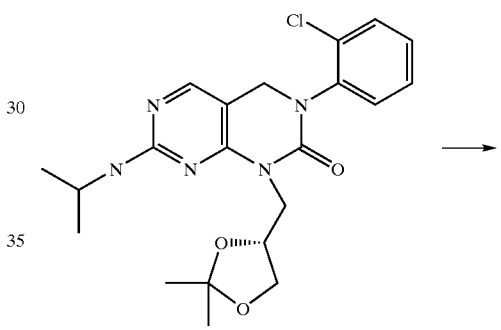

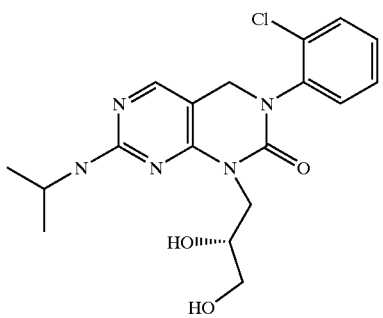

To a solution of 0.4 g (0.93 mmol) of the isopropyl amine adduct prepared above in methanol (15 mL) and water (7 mL) was added 0.05 g p-toluenesulfonic acid and the mixture was heated to 50° C. After 16 hours, the methanol was removed under reduced pressure and the resulting aqueous solution was extracted with ethyl acetate. The organic fractions were washed with 5% aqueous sodium bicarbonate solution and brine, then dried over sodium sulfate, concentrated and purified by flash chromatography (gradient elution: 40–100% ethyl acetate/hexane) to give 0.2 g of product, 3-(2-chlorophenyl)-1-[(2S)-2,3-dihydroxyethyl]-7-isopropylamino-3,4-dihydropyrimido[4,5-d]pyrimidin-2(1H)-one (mass spec. M⁺=391.Mpt. 130.8–134.7)

Example 9

This example illustrates the preparation of 3-(2-chlorophenyl)-1-[(2R)-2,3-dihydroxyethyl]-7-isopropylamino-3,4-dihydropyrimido[4,5-d]pyrimidin-2(1H)-one Step 1

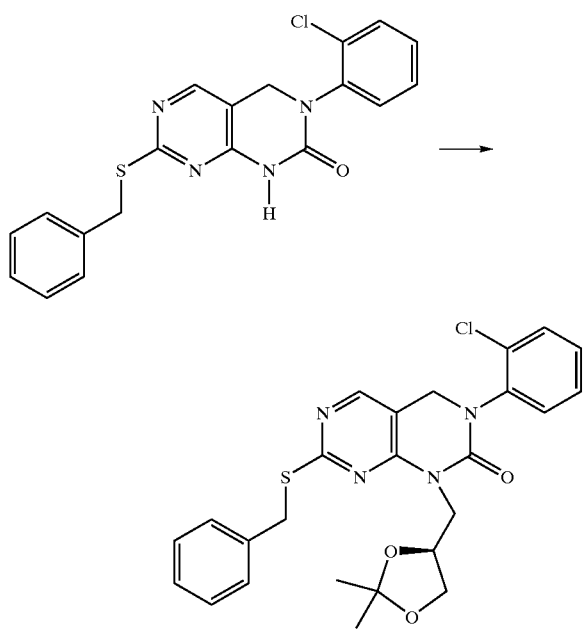

A mixture of 1.0 g (2.6 mmol) of 7-benzylthio-3-(2-chlorophenyl)-3,4-dihydro-pyrimido[4,5-d]pyrimidin-2(1H)-one, 1.5 g (5.2 mmol) D-α,β-isopropylidene glycerol-γ-tosylate and 1.44 g (10.4 mmol) of potassium carbonate was stirred in DMF (25 mL) and heated at 80° C. under nitrogen atmosphere. After 16 h, the reaction mixture was cooled to room temperature, poured in to a brine solution, extracted with ethyl acetate and dried over sodium sulfate. The solution was concentrated under vacuum, purified by flash chromatography (eluting with 40% EtOAc/Hexane) to give 1.2 g of the isopropylidene ketal adduct as an oil.

Step 2

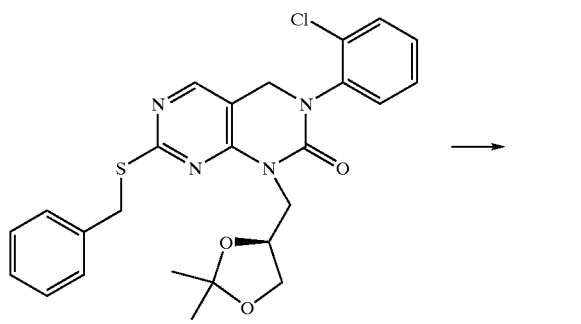

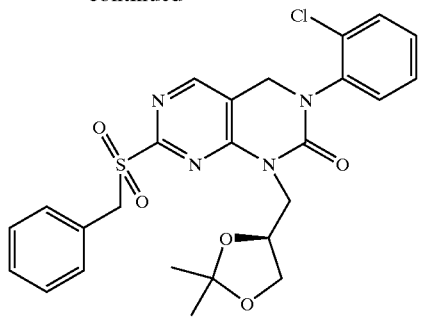

To a solution of 1.2 g (2.4 mmol) of isopropylidene ketal adduct prepared above in methylene chloride (30 mL), cooled in a wet ice bath under nitrogen atmosphere, was added 1.1 g (5.6 mmol) of m-chloroperbenzoic acid portionwise. The resulting suspension was stirred and allowed to warm to room temperature. After 6 hours, the reaction mixture was cooled in a wet ice bath and a 10% aqueous solution of sodium bisulfite (50 mL) was added dropwise. The mixture was stirred for 30 minutes and the layers were separated. The aqueous layer was extracted with methylene chloride and the combined organic fractions were washed with brine, dried over sodium sulfate and concentrated to dryness. The residue was purified by flash chromatography (gradient elution: ethyl acetate-10% methanol/ethyl acetate). The sulfone product was isolated (1.1 g) as a foam. (mass spec. MH$^+$=529).

Step 3

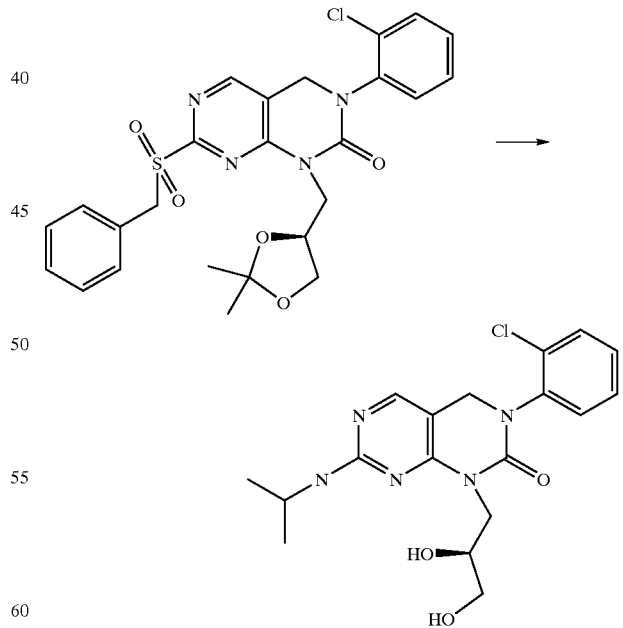

A solution of 0.22 g (0.42 mmol) of the sulfone prepared above in 5 mL of isopropylamine was heated at 40° C. under nitrogen atmosphere. After 3 hours, the reaction mixture was cooled to room temperature, concentrated to dryness and purified by flash chromatography (elution with ethyl acetate) to give 0.088 g of the product, 3-(2-chloro-phenyl)-1-[(2R)-2,3-dihydroxyethyl]-7-isopropylamino-3,4-dihydropyrimido[4,5-d]-pyrimidin-2(1H)-one as a foam. (mass spec. MH$^+$=392).

Example 10

This example illustrates the preparation of 7-isopropylamino-3-(2-chloro-phenyl)-1-(2-piperidinyl-ethyl)-3,4-dihydropyrimido[4,5-d]pyrimidin-2(1H)-one.

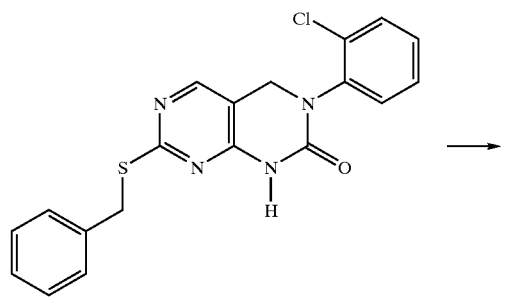

7-benzylthio-3-(2-chlorophenyl)-3,4-dihydropyrimido[4,5-d]pyrimidin-2(1H)-one, (500 mg, 1.31 mmol) was taken up in 2 mL THF with 1-piperidineethanol (0.173 mL, 1.31 mmol), triphenylphosphine (343 mg, 1.31 mmol), and DEAD (0.21 mL, 1.31 mmol) and stirred at room temperature for 4 days, then purified by chromatography on silica gel with 2–5% methanol/dichloromethane as eluant, to provide 350 mg of the N-(2-piperidinylethyl) adduct.

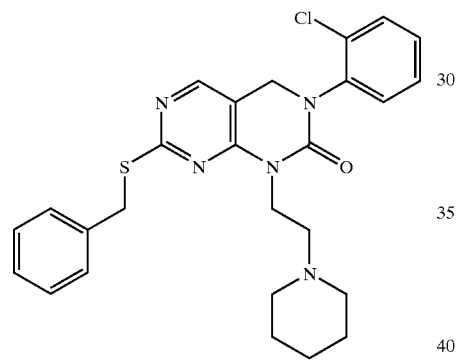

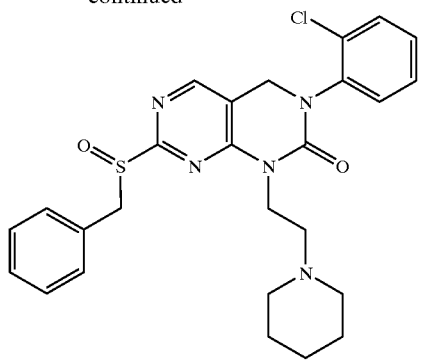

Oxidation of the sulfide was accomplished using m-CPBA (0.201 g, 0,708 mmol) in dichloromethane with stirring at rt for 1 hour. The reaction was quenched with 0.5 mL 25% aqueous sodium sulfite and extracted with dichloromethane. The extract was dried with magnesium sulfate and concentrated in vacuo to provide the sulfoxide, which was used without purification.

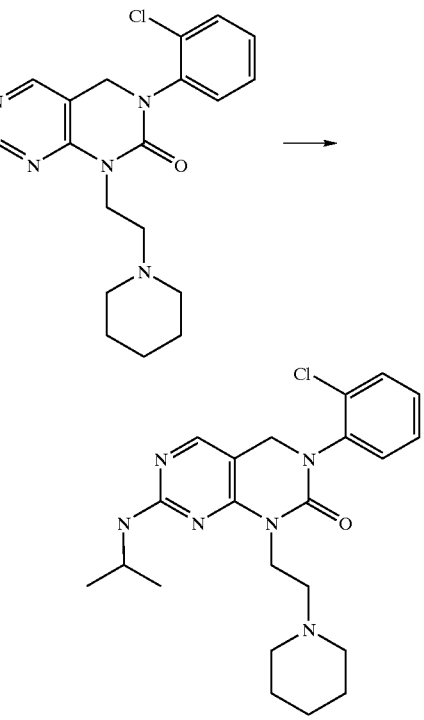

The crude sulfoxide was taken up in 5 mL isopropylamine and stirred at 40° C. overnight, then 80 C. for 4 days. The mixture was purified by chromatography on silica gel using 1–10% methanol/dichloromethane as eluant to provide the amine (48 mg, 0.112 mmol). The purified product was taken up in ethyl acetate and treated with 1 equivalent HCl/Et$_2$O to precipitate the HCl salt of 7-isopropylamino-3-(2-chlorophenyl)-1-(2-piperidinyl-ethyl)-3,4-dihydropyrimido-[4,5-d]pyrimidin-2(1H)-one.

Example 11

In vitro p38 MAP Kinase Inhibition Assay

This example illustrates a p38 (MAP) kinase in vitro assay useful for evaluating the compounds of the present invention.

The p-38 MAP kinase inhibitory activity of compounds of this invention in vitro was determined by measuring the transfer of the γ-phosphate from γ-$^{33}$P-ATP by p-38 kinase to Myelin Basic Protein (MBP), using a minor modification of the method described in Ahn, et al., *J. Biol. Chem.* 266:4220–4227 (1991).

The phosphorylated form of the recombinant p38 MAP kinase was co-expressed with SEK-1 and MEKK in *E. Coli* (see, Khokhlatchev, et al., *J. Biol. Chem.* 272:11057–11062 (1997)) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium ortho-vanadate, 1 mM dithiothreitol, 40 mM magnesium chloride). Test compound dissolved in DMSO or only DMSO (control) was added and the samples were incubated for 10 minutes at 30° C. The kinase reaction was initiated by the addition of a substrate cocktail containing MBP and γ-$^{33}$P-ATP. After incubating for an additional 20 minutes at 30° C., the reaction was terminated by adding 0.75% phosphoric acid. The phosphorylated MBP was then separated from the residual γ-$^{33}$P-ATP using a phosphocellulose membrane (Millipore, Bedfrod, Mass.) and quantitated using a scintillation counter (Packard, Meriden, Conn.).

The p38 inhibitory activities (expressed as $IC_{50}$, the concentration causing 50% inhibition of the p38 enzyme being assayed) of the compounds of the invention described in Examples 1–4 were less than 10 μM.:

Example 12

In vitro TNF Inhibition Assay

This example illustrates an in vitro assay to evaluate the inhibition of LPS-induced TNF-α production in THP1 cells.

The ability of the compounds of this invention to inhibit the TNF-α release was determined using a minor modification of the methods described in Blifeld, et al. *Transplantation,* 51:498–503 (1991).

(a) Induction of TNF Biosynthesis

THP-1 cells were suspended in culture medium [RPMI (Gibco-BRL, Gailthersburg, Md.) containing 15% fetal bovine serum, 0.02 mM 2-mercaptoethanol], at a concentration of 2.5×10$^6$ cells/mL and then plated in 96 well plate (0.2 mL aliquots in each well). Test compounds were dissolved in DMSO and then diluted with the culture medium such that the final DMSO concentration was 5%. Twenty five μL aliquots of test solution or only medium with DMSO (control) were added to each well. The cells were incubated for 30 minutes at 37° C. LPS (Sigma, St. Louis, Mo.) was added to the wells at a final concentration of 0.5 μg/mL, and cells were incubated for an additional 2 hours. At the end of the incubation period, culture supernatants were collected and the amount of TNF-α present was determined using an ELISA assay as described below.

(b) ELISA Assay:

The amount of human TNF-α present was determined by a specific trapping ELISA assay using two anti-TNF-α antibodies (2TNF-H12 and 2TNF-H34) described in Reimund, J. M., et al. *GUT.* Vol. 39(5), 684–689 (1996).

Polystyrene 96-well plates were coated with 50 μl per well of antibody 2TNF-H12 in PBS (10 μg/mL) and incubated in a humidified chamber at 4° C. overnight. The plates were washed with PBS and then blocked with 5% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay began at 10 ng/mL followed by 6 half log serial dilutions.

Twenty five μL aliquots of the above culture supernatants or TNF standards or only medium (control) were mixed with 25 μL aliquots of biotinylated monoclonal antibody 2TNF-H34 (2 μg/mL in PBS containing 0.1% BSA) and then added to each well. The samples were incubated for 2 hours at room temperature with gentle shaking and then washed 3 times with 0.1% BSA in PBS. 50 μl of peroxidase-streptavidin (Zymed, South San Francisco, Calif.) solution containing 0.416 μg/mL of peroxidase-streptavidin and 0.1% BSA in PBS was added to each well. The samples were incubated for an additional 1 hour at room temperature and then washed 4 times with 0.1% BSA in PBS. Fifty μL of O-phenylene-diamine solution (1 μg/mL O-phenylenediamine and 0.03% hydrogen peroxide in 0.2M citrate buffer pH 4.5) was added to each well and the samples were incubated in the dark at room temperature for 30 minutes. Optical density of the sample and the reference were read at 450 nm and 650 nm, respectively. TNF-α levels were determined from a graph relating the optical density at 450 nm to the concentration used.

The $IC_{50}$ value was defined as the concentration of the test compound corresponding to half-maximal reduction in 450 nm absorbance.

Example 13

This example illustrates an in vivo assay to evaluate the inhibition of LPS-induced TNF-α production in mice (or rats).

The ability of the compounds of this invention to inhibit the TNF-α release, in vivo, was determined using a minor modification of the methods described in described in Zanetti, et. al., *J. Immunol.,* 148:1890 (1992) and Sekut, et. al., *J. Lab. Clin. Med.,* 124:813 (1994).

Female BALB/c mice weighing 18–21 grams (Charles River, Hollister, Calif.) were acclimated for one week. Groups containing 8 mice each were dosed orally either with the test compounds suspended or dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 minutes, the mice were injected intraperitoneally with 20 μg of LPS (Sigma, St. Louis, Mo.). After 1.5 hours, the mice were sacrificed by $CO_2$ inhalation and blood was harvested by cardiocentesis. Blood was clarified by centrifugation at 15,600×g for 5 minutes, and sera were transferred to clean tubes and frozen at −20° C. until analyzed for TNF-α by ELISA assay (Biosource International, Camarillo, Calif.) following the manufacturer's protocol.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent

What is claimed is:

1. A compound represented by formula I:

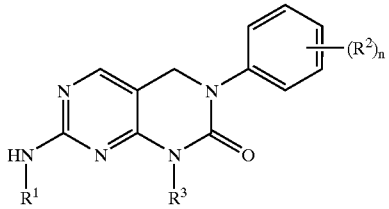

(I)

wherein
the subscript n is an integer of from 0 to 3;
$R^1$ is a member selected from the group consisting of hydrogen, alkyl, alkenyl, alkynyl, alkylcarbonyl, cycloalkyl, cycloalkenyl, cycloalkylalkyl, cycloalkylalkenyl, cycloalkylalkynyl and aralkyl;
each $R^2$ is independently selected from the group consisting of alkyl, halo, heteroalkyl and vinyl; and
$R^3$ is a member selected from the group consisting of heteroalkyl, heteroalkenyl, heteroalkynyl, heteroalkylcarbonyl, heterosubstituted cycloalkyl, heterosubstituted cycloalkylalkyl, heterosubstituted cycloalkylalkenyl, heterosubstituted cycloalkylalkynyl, heteroalkylsubstituted cycloalkyl, heterocyclyl, heterocyclylalkyl, arylheteroalkyl, heteroarylheteroalkyl, -(alkylene)-C(O)$R^{31}$ and -(heteroalkylene)-C(O)$R^{31}$; wherein
$R^{31}$ is a member selected from the group consisting of alkyl, haloalkyl, hydroxy, alkoxy, amino, monsubstituted amino, disubstituted amino, cycloalkyl, cycloalkylalkyl, aryl, aralkyl, heteroaryl, and heteroaralkyl;
or its pharmaceutically acceptable salts.

2. A compound in accordance with claim 1, wherein n is an integer of from 1 to 2, and each $R^2$ is independently selected from the group consisting of halo and alkyl.

3. A compound in accordance with claim 2, wherein n is an integer of from 1 to 2, and each $R^2$ is independently a halogen.

4. A compound in accordance with claim 3, wherein —$(R^2)_n$ represents 2-halo or 2,6-dihalo.

5. A compound in accordance with claim 1, wherein $R^3$ is heteroalkyl.

6. A compound in accordance with claim 1, wherein $R^3$ is heterocyclyl.

7. A compound in accordance with claim 1, wherein $R^1$ is a member selected from the group consisting of hydrogen, alkyl, cycloalkyl and aralkyl.

8. A compound in accordance with claim 7, wherein $R^1$ is alkyl.

9. A compound in accordance with claim 7, wherein $R^1$ is cycloalkyl.

10. A compound in accordance with claim 7, wherein $R^1$ is alkyl or cycloalkyl, $R^2$ is halo, $R^3$ is heteroalkyl and n is 1 or 2.

11. A compound in accordance with claim 7, wherein $R^1$ is alkyl or cycloalkyl, $R^2$ is halo, $R^3$ is heterocyclyl and n is 1 or 2.

12. A compound in accordance with claim 7, wherein $R^1$ is alkyl or cycloalkyl, $R^2$ is halo, $R^3$ is heterosubstituted cycloalkyl and n is 1 or 2.

13. A compound in accordance with claim 1, wherein $R^1$ is isopropyl, $R^2$ is halo and n is 1 or 2.

14. A composition comprising a pharmaceutically acceptable excipient and a compound represented by formula (I):

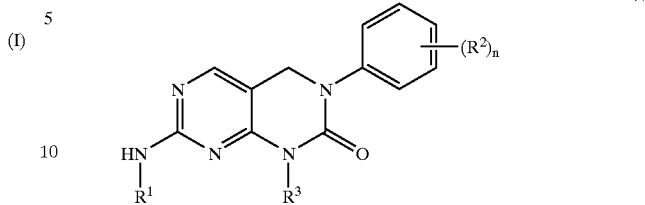

(I)

wherein
the subscript n is an integer of from 0 to 3;
$R^1$ is a member selected from the group consisting of hydrogen, alkyl, alkenyl, alkynyl, alkylcarbonyl, cycloalkyl, cycloalkylalkyl, cycloalkylalkenyl, cycloalkylalkynyl and aralkyl;
each $R^2$ is independently selected from the group consisting of alkyl, halo, heteroalkyl and vinyl; and
$R^3$ is a member selected from the group consisting of heteroalkyl, heteroalkenyl, heteroalkynyl, heteroalkylcarbonyl, heterosubstituted cycloalkyl, heterosubstituted cycloalkylalkyl, heterosubstituted cycloalkylalkenyl, heterosubstituted cycloalkylalkynyl, heterosubstituted cycloalkyl, heterocyclyl, heterocyclylalkyl, arylheteroalkyl, heteroarylheteroalkyl, -(alkylene)-C(O)$R^{31}$ and -(heteroalkylene)-C(O)$R^{31}$; wherein
$R^{31}$ is a member selected from the group consisting of alkyl, haloalkyl, hydroxy, alkoxy, amino, monsubstituted amino, disubstituted amino, cycloalkyl, cycloalkylalkyl, aryl, aralkyl, heteroaryl, and heteroaralkyl;
or its pharmaceutically acceptable salts.

15. A method for the preparation of a compound of claim 1, said method comprising:
(a) treating a compound of formula II

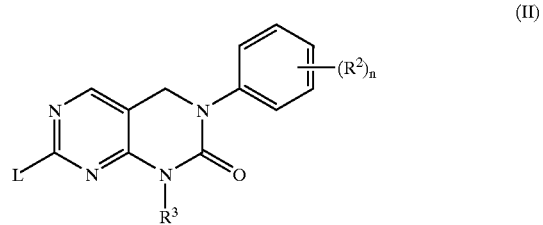

(II)

wherein n, $R^2$ and $R^3$ have the meanings provided in claim 1, any interfering reactive group present is in protected form, and L is a leaving group, with an amine of formula III

$R^1$—NH$_2$ (III)

wherein $R^1$ has the meaning provided in claim 1, any interfering reactive group present is in protected form, and deprotecting the protected reactive group present in the reaction product.

16. A method of treating a p38 mediated disorder in a patient, said method comprising administering to said patient at least one compound according to claim 1, wherein said p38 mediated disorder is selected from the group consisting of arthritis, Crohns disease, irritable bowel syndrome, adult respiratory distress syndrome, chronic obstructive pulmonary disease, asthma, Alzheimer's disease, psoriasis, dermatitis, osteoporosis, graft vs. host reaction, allograft rejection, atherosclerosis, thrombosis, congestive heart failure, and cardiac reperfusion injury.

17. A compound represented by formula I:

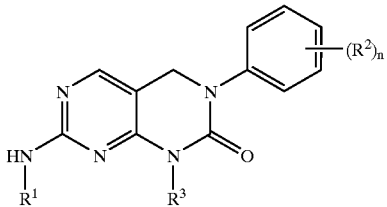

(I)

wherein
the subscript n is an integer of from 0 to 3;
$R^1$ is a member selected from the group consisting of hydrogen, alkyl, alkenyl, alkynyl, alkylcarbonyl, cycloalkyl, cycloalkenyl, cycloalkylalkyl, cycloalkylalkenyl, cycloalkylalkynyl and aralkyl;
each $R^2$ is independently selected from the group consisting of alkyl, halo, heteroalkyl and vinyl; and
$R^3$ is a member selected from the group consisting of heteroalkylcarbonyl, heterosubstituted cycloalkylalkyl, heterosubstituted cycloalkylalkenyl, heterosubstituted cycloalkylalkynyl, heteroalkylsubstituted cycloalkyl, arylheteroalkyl, heteroarylheteroalkyl, -(alkylene)-C(O)$R^{31}$ and -(heteroalkylene)-C(O)$R^{31}$; wherein
$R^{31}$ is a member selected from the group consisting of alkyl, haloalkyl, hydroxy, alkoxy, amino, monsubstituted amino, disubstituted amino, cycloalkyl, cycloalkylalkyl, aryl, aralkyl, heteroaryl, and heteroaralkyl;
or its pharmaceutically acceptable salts.

18. A compound in accordance with claim 17 wherein n is an integer of from 1 to 2, and each $R^2$ is independently selected from the group consisting of halo and alkyl.

19. A compound in accordance with claim 18 wherein n is an integer of from 1 to 2, and each $R^2$ is independently a halogen.

20. compound in accordance with claim 19, wherein —($R^2$)$_n$ represents 2-halo or 2,6-dihalo.

21. A compound in accordance with claim 17, wherein $R^1$ is alkyl or cycloalkyl.

22. A compound in accordance with claim 21, wherein $R^1$ is isopropyl.

* * * * *